(12) United States Patent
Badawi et al.

(10) Patent No.: US 11,865,041 B2
(45) Date of Patent: *Jan. 9, 2024

(54) INTRAOCULAR IMPLANTS AND METHODS AND KITS THEREFOR

(71) Applicant: Sight Sciences, Inc., Menlo Park, CA (US)

(72) Inventors: David Y. Badawi, Glenview, IL (US); Paul Badawi, Menlo Park, CA (US)

(73) Assignee: SIGHT SCIENCES, INC., Menlo Park, CA (US)

( * ) Notice: Subject to any disclaimer, the term of this patent is extended or adjusted under 35 U.S.C. 154(b) by 850 days.

This patent is subject to a terminal disclaimer.

(21) Appl. No.: 16/526,832

(22) Filed: Jul. 30, 2019

(65) Prior Publication Data

US 2020/0121503 A1 Apr. 23, 2020

Related U.S. Application Data

(63) Continuation of application No. 15/340,911, filed on Nov. 1, 2016, now Pat. No. 10,398,597, which is a
(Continued)

(51) Int. Cl.
*A61F 9/007* (2006.01)
*A61F 9/00* (2006.01)

(52) U.S. Cl.
CPC ........ *A61F 9/00781* (2013.01); *A61F 9/0017* (2013.01); *A61F 2210/0004* (2013.01);
(Continued)

(58) Field of Classification Search
CPC .......... A61F 9/00781; A61F 2210/0014; A61F 9/0017
(Continued)

(56) References Cited

U.S. PATENT DOCUMENTS 3,159,161 A 12/1964 Ness
4,068,664 A 1/1978 Sharp et al.
(Continued)

FOREIGN PATENT DOCUMENTS

CA 2244646 A1 2/1999
CA 2778452 A1 4/2011
(Continued)

OTHER PUBLICATIONS

Boyle, E.L. (Feb. 1, 2006). "New Glaucoma Devices Take Different Approaches to IOP Lowering," *Ocular Surgery News U.S. Edition*, located at <http://www.osnsupersite.com/view.aspx?rid=12436>, last visited on Apr. 23, 2012, 4 pages, revisited on Apr. 19, 2016, 5 pages.
(Continued)

*Primary Examiner* — Leslie R Deak
(74) *Attorney, Agent, or Firm* — Cooley LLP

(57) ABSTRACT

Devices, methods and kits are described for reducing intraocular pressure. The devices include a support that is implantable within Schlemm's canal and maintains the patency of the canal without substantially interfering with transmural fluid flow across the canal. The devices utilize the natural drainage process of the eye and can be implanted with minimal trauma to the eye. Kits include a support and an introducer for implanting the support within Schlemm's canal. Methods include implanting a support within Schlemm's canal, wherein the support is capable of maintaining the patency of the canal without substantial interference with transmural fluid flow across the canal.

20 Claims, 15 Drawing Sheets

Related U.S. Application Data continuation of application No. 13/445,816, filed on Apr. 12, 2012, now Pat. No. 9,486,361, which is a continuation of application No. 12/695,053, filed on Jan. 27, 2010, now Pat. No. 8,287,482, which is a continuation of application No. 11/475,523, filed on Jun. 26, 2006, now Pat. No. 7,909,789.

(52) U.S. Cl.
CPC ............... *A61F 2210/0014* (2013.01); *A61F 2250/0067* (2013.01)

(58) Field of Classification Search
USPC .............. 604/8, 9, 264; 623/23.64, 23.7
See application file for complete search history.

(56) References Cited

U.S. PATENT DOCUMENTS

| | | | |
|---|---|---|---|
| 4,457,757 A | 7/1984 | Molteno | |
| 1,501,274 A | 2/1985 | Skjaerpe | |
| 4,553,545 A | 11/1985 | Maass et al. | |
| 4,719,825 A | 1/1988 | LaHaye et al. | |
| 4,863,457 A | 9/1989 | Lee | |
| 1,936,825 A | 6/1990 | Ungerleider | |
| 4,957,505 A | 9/1990 | McDonald | |
| 5,092,837 A | 3/1992 | Ritch et al. | |
| 5,180,362 A | 1/1993 | Worst | |
| 5,284,476 A | 2/1994 | Koch | |
| 5,358,473 A | 10/1994 | Mitchell | |
| 5,360,399 A | 11/1994 | Stegmann | |
| 5,368,572 A | 11/1994 | Shirota | |
| 5,486,165 A | 1/1996 | Stegmann | |
| 5,540,657 A | 7/1996 | Kurjan et al. | |
| 5,558,634 A | 9/1996 | Mitchell | |
| 5,569,197 A | 10/1996 | Helmus et al. | |
| 5,626,558 A | 5/1997 | Suson | |
| 5,639,278 A | 6/1997 | Dereume et al. | |
| 5,792,099 A | 8/1998 | DeCamp et al. | |
| 5,792,103 A | 8/1998 | Schwartz et al. | |
| 5,868,697 A | 2/1999 | Richter et al. | |
| 6,036,678 A | 3/2000 | Giungo | |
| 6,050,970 A | 4/2000 | Baerveldt | |
| 6,050,999 A | 4/2000 | Paraschac et al. | |
| 6,299,603 B1 | 10/2001 | Hecker et al. | |
| 6,309,375 B1 | 10/2001 | Glines et al. | |
| 6,375,642 B1 | 4/2002 | Grieshaber et al. | |
| 6,450,984 B1 | 9/2002 | Lynch et al. | |
| 6,491,670 B1 | 12/2002 | Toth et al. | |
| 6,494,857 B1 | 12/2002 | Neuhann | |
| 6,508,779 B1 | 1/2003 | Suson | |
| 6,524,275 B1 | 2/2003 | Lynch et al. | |
| 6,533,768 B1 | 3/2003 | Hill | |
| 6,616,996 B1 | 9/2003 | Keith et al. | |
| 6,626,858 B2 | 9/2003 | Lynch et al. | |
| 6,638,239 B1 | 10/2003 | Bergheim et al. | |
| 6,666,841 B2 | 12/2003 | Gharib et al. | |
| 6,726,676 B2 | 4/2004 | Stegmann et al. | |
| 6,730,056 B1 | 5/2004 | Ghaem et al. | |
| 6,736,791 B1 | 5/2004 | Tu et al. | |
| 6,780,164 B2 | 8/2004 | Bergheim et al. | |
| 6,783,544 B2 | 8/2004 | Lynch et al. | |
| 6,840,952 B2 | 1/2005 | Saker et al. | |
| 6,843,792 B2 | 1/2005 | Nishtala et al. | |
| 6,893,415 B2 | 5/2005 | Madsen et al. | |
| 6,955,656 B2 | 10/2005 | Bergheim et al. | |
| 6,962,573 B1 | 11/2005 | Wilcox | |
| 7,094,225 B2 | 8/2006 | Tu et al. | |
| 7,135,009 B2 | 11/2006 | Tu et al. | |
| 7,186,232 B1 | 3/2007 | Smedley et al. | |
| 7,192,412 B1 | 3/2007 | Zhou et al. | |
| 7,207,980 B2 | 4/2007 | Christian et al. | |
| 7,273,475 B2 | 9/2007 | Tu et al. | |
| 7,297,130 B2 | 11/2007 | Bergheim et al. | |
| 7,331,984 B2 | 2/2008 | Tu et al. | |
| 7,488,303 B1 | 2/2009 | Haffner et al. | |
| 7,588,597 B2 | 9/2009 | Frid | |
| 7,713,228 B2 | 5/2010 | Robin | |
| 7,740,604 B2 | 6/2010 | Schieber et al. | |
| 7,806,847 B2 | 10/2010 | Wilcox | |
| 7,850,637 B2 | 12/2010 | Lynch et al. | |
| 7,867,205 B2 | 1/2011 | Bergheim et al. | |
| 7,909,789 B2 * | 3/2011 | Badawi ................ | A61F 9/0017 604/9 |
| 7,951,155 B2 | 5/2011 | Smedley et al. | |
| 7,967,772 B2 | 6/2011 | McKenzie et al. | |
| 8,034,105 B2 | 10/2011 | Stegmann et al. | |
| 8,075,511 B2 | 12/2011 | Tu et al. | |
| 8,109,896 B2 | 2/2012 | Nissan et al. | |
| 8,123,729 B2 | 2/2012 | Yamamoto et al. | |
| 8,133,208 B2 | 3/2012 | Hetherington | |
| 8,137,307 B2 | 3/2012 | Tennican et al. | |
| 8,152,752 B2 | 4/2012 | Lynch et al. | |
| 8,172,899 B2 | 5/2012 | Silvestrini et al. | |
| 8,267,882 B2 | 9/2012 | Euteneuer et al. | |
| 8,273,050 B2 | 9/2012 | Bergheim et al. | |
| 8,282,592 B2 | 10/2012 | Schieber et al. | |
| 8,287,482 B2 | 10/2012 | Badawi et al. | |
| 8,333,742 B2 | 12/2012 | Bergheim et al. | |
| 8,337,509 B2 | 12/2012 | Schieber et al. | |
| 8,348,924 B2 | 1/2013 | Christian et al. | |
| 8,366,653 B2 | 2/2013 | Shareef et al. | |
| 8,372,026 B2 | 2/2013 | Schieber et al. | |
| 8,388,568 B2 | 3/2013 | Lynch et al. | |
| 8,403,920 B2 | 3/2013 | Lind et al. | |
| 8,414,518 B2 | 4/2013 | Schieber et al. | |
| 8,414,636 B2 | 4/2013 | Nabulsi et al. | |
| 8,425,449 B2 | 4/2013 | Wardle et al. | |
| 8,425,450 B2 | 4/2013 | Wilcox | |
| 8,439,972 B2 | 5/2013 | Badawi et al. | |
| 8,444,589 B2 | 5/2013 | Silvestrini | |
| 8,491,549 B2 | 7/2013 | Conston et al. | |
| 8,512,321 B2 | 8/2013 | Baerveldt et al. | |
| 8,512,404 B2 | 8/2013 | Frion et al. | |
| 8,529,622 B2 | 9/2013 | Badawi et al. | |
| 8,540,659 B2 | 9/2013 | Berlin | |
| 8,540,681 B2 | 9/2013 | Hetherington | |
| 8,540,761 B2 | 9/2013 | Rabkin et al. | |
| 8,545,431 B2 | 10/2013 | Rickard | |
| 8,568,391 B2 | 10/2013 | Kearns et al. | |
| 8,617,094 B2 | 12/2013 | Smedley et al. | |
| 8,657,776 B2 | 2/2014 | Wardle et al. | |
| 8,663,150 B2 | 3/2014 | Wardle et al. | |
| 8,715,266 B2 | 5/2014 | Bos | |
| 8,734,377 B2 | 5/2014 | Schieber et al. | |
| 8,747,299 B2 | 6/2014 | Grieshaber | |
| 8,771,217 B2 | 7/2014 | Lynch et al. | |
| 8,801,648 B2 | 8/2014 | Bergheim et al. | |
| 8,808,222 B2 | 8/2014 | Schieber et al. | |
| 8,827,990 B2 | 9/2014 | Van Valen et al. | |
| 8,852,137 B2 | 10/2014 | Horvath et al. | |
| 8,876,898 B2 | 11/2014 | Badawi et al. | |
| 8,888,734 B2 | 11/2014 | Nissan et al. | |
| 8,894,603 B2 | 11/2014 | Badawi et al. | |
| 8,926,546 B2 | 1/2015 | Wilcox | |
| 8,961,447 B2 | 2/2015 | Schieber et al. | |
| 9,039,650 B2 | 5/2015 | Schieber et al. | |
| 9,044,301 B1 | 6/2015 | Pinchuk et al. | |
| 9,050,169 B2 | 6/2015 | Schieber et al. | |
| 9,066,750 B2 | 6/2015 | Wardle et al. | |
| 9,066,783 B2 | 6/2015 | Euteneuer et al. | |
| 9,095,412 B2 | 8/2015 | Badawi et al. | |
| 9,107,729 B2 | 8/2015 | Sorensen et al. | |
| 9,125,723 B2 | 9/2015 | Horvath et al. | |
| 9,155,655 B2 | 10/2015 | Schieber et al. | |
| 9,192,516 B2 | 11/2015 | Horvath et al. | |
| 9,211,213 B2 | 12/2015 | Wardle et al. | |
| 9,216,109 B2 | 12/2015 | Badawi et al. | |
| 9,220,632 B2 | 12/2015 | Smedley et al. | |
| 9,226,850 B2 | 1/2016 | Baerveldt et al. | |
| 9,226,852 B2 | 1/2016 | Schieber et al. | |
| 9,301,875 B2 | 4/2016 | Tu et al. | |
| 9,326,891 B2 | 5/2016 | Horvath et al. | |
| 9,339,514 B2 | 5/2016 | Bos et al. | |

(56) References Cited

U.S. PATENT DOCUMENTS

| | | | |
|---|---|---|---|
| 9,351,874 B2 | 5/2016 | Schieber et al. |
| 9,358,155 B2 | 6/2016 | Sorensen et al. |
| 9,358,156 B2 | 6/2016 | Wardle et al. |
| 9,370,443 B2 | 6/2016 | Badawi et al. |
| 9,381,111 B2 | 7/2016 | Hickingbotham et al. |
| 9,402,767 B2 | 8/2016 | Schieber et al. |
| 9,486,361 B2 | 11/2016 | Badawi et al. |
| 9,492,319 B2 | 11/2016 | Grieshaber et al. |
| 9,492,320 B2 | 11/2016 | Lynch et al. |
| 9,510,973 B2 | 12/2016 | Wardle |
| 9,855,167 B2 | 1/2018 | Badawi et al. |
| 9,889,258 B2 | 2/2018 | Bengtsson et al. |
| 9,895,258 B2 | 2/2018 | Badawi et al. |
| 10,154,924 B2 | 12/2018 | Clauson et al. |
| 10,179,066 B2 | 1/2019 | Badawi et al. |
| 10,299,958 B2 | 5/2019 | Badawi et al. |
| 10,314,742 B2 | 6/2019 | Badawi et al. |
| 10,398,597 B2 * | 9/2019 | Badawi ............... A61F 9/00781 |
| 10,406,030 B2 | 9/2019 | Badawi et al. |
| 10,857,027 B2 | 12/2020 | Badawi et al. |
| 10,888,453 B2 | 1/2021 | Badawi et al. |
| 10,905,591 B1 | 2/2021 | Ianchulev |
| 11,090,188 B2 | 8/2021 | Badawi et al. |
| 11,116,660 B2 | 9/2021 | Badawi et al. |
| 11,166,847 B2 | 11/2021 | Badawi et al. |
| 11,259,961 B2 | 3/2022 | Ianchulev |
| 11,344,447 B2 | 5/2022 | Badawi et al. |
| 11,389,327 B2 | 7/2022 | Badawi et al. |
| 11,389,328 B2 | 7/2022 | Badawi et al. |
| 11,419,762 B2 | 8/2022 | Ianchulev |
| 11,471,324 B2 | 10/2022 | Badawi et al. |
| 11,504,270 B1 | 11/2022 | Badawi et al. |
| 11,617,679 B2 | 4/2023 | Badawi et al. |
| 2001/0014788 A1 | 8/2001 | Morris |
| 2002/0013546 A1 | 1/2002 | Grieshaber et al. |
| 2002/0013572 A1 | 1/2002 | Berlin |
| 2002/0055753 A1 | 5/2002 | Silvestrini |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2002/0165478 A1 | 11/2002 | Gharib et al. |
| 2003/0060447 A1 | 3/2003 | Karakelle et al. |
| 2003/0060752 A1 | 3/2003 | Bergheim et al. |
| 2003/0060873 A1 | 3/2003 | Gertner et al. |
| 2003/0120200 A1 | 6/2003 | Bergheim et al. |
| 2003/0181848 A1 | 9/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0044310 A1 | 3/2004 | Suzuki |
| 2004/0102719 A1 | 5/2004 | Keith et al. |
| 2004/0102729 A1 | 5/2004 | Haffner et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0254519 A1 | 12/2004 | Tu et al. |
| 2004/0254520 A1 * | 12/2004 | Porteous ............ A61F 9/00781 |
| | | 977/883 |
| 2004/0254521 A1 | 12/2004 | Simon |
| 2004/0260228 A1 | 12/2004 | Lynch et al. |
| 2005/0038334 A1 | 2/2005 | Lynch et al. |
| 2005/0055082 A1 | 3/2005 | Ben Muvhar et al. |
| 2005/0090807 A1 | 4/2005 | Lynch et al. |
| 2005/0101967 A1 | 5/2005 | Weber et al. |
| 2005/0125003 A1 | 6/2005 | Pinchuk et al. |
| 2005/0165363 A1 | 7/2005 | Judson et al. |
| 2005/0171507 A1 | 8/2005 | Christian |
| 2005/0192527 A1 | 9/2005 | Gharib et al. |
| 2005/0209549 A1 | 9/2005 | Bergheim et al. |
| 2005/0250788 A1 | 11/2005 | Tu et al. |
| 2005/0266047 A1 | 12/2005 | Tu et al. |
| 2005/0267555 A1 | 12/2005 | Marnfeldt et al. |
| 2005/0277864 A1 | 12/2005 | Haffner et al. |
| 2005/0288619 A1 | 12/2005 | Gharib et al. |
| 2006/0032507 A1 | 2/2006 | Tu |
| 2006/0034891 A1 | 2/2006 | Lawin et al. |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0149194 A1 | 7/2006 | Conston |
| 2006/0155300 A1 | 7/2006 | Stamper et al. |
| 2006/0173077 A1 | 8/2006 | Cagle |
| 2006/0173397 A1 | 8/2006 | Tu et al. |
| 2006/0173446 A1 | 8/2006 | Dacquay et al. |
| 2006/0195055 A1 | 8/2006 | Bergheim et al. |
| 2006/0195056 A1 | 8/2006 | Bergheim et al. |
| 2006/0195187 A1 | 8/2006 | Stegmann et al. |
| 2006/0200113 A1 | 9/2006 | Haffner et al. |
| 2006/0217741 A1 | 9/2006 | Ghannoum |
| 2006/0241580 A1 | 10/2006 | Mittelstein et al. |
| 2007/0073275 A1 | 3/2007 | Conston et al. |
| 2007/0106236 A1 | 5/2007 | Coroneo |
| 2007/0191863 A1 | 8/2007 | De Juan, Jr. et al. |
| 2007/0260173 A1 | 11/2007 | Boukhny et al. |
| 2007/0276420 A1 | 11/2007 | Sorensen et al. |
| 2008/0004596 A1 | 1/2008 | Yun et al. |
| 2008/0058704 A1 | 3/2008 | Hee et al. |
| 2008/0058760 A1 | 3/2008 | Agerup |
| 2008/0082078 A1 | 4/2008 | Berlin |
| 2008/0108934 A1 | 5/2008 | Berlin |
| 2008/0300574 A1 | 12/2008 | Belson et al. |
| 2009/0036819 A1 | 2/2009 | Tu et al. |
| 2009/0036827 A1 | 2/2009 | Cazzini |
| 2009/0043321 A1 | 2/2009 | Conston et al. |
| 2009/0082860 A1 | 3/2009 | Schieber et al. |
| 2009/0082862 A1 | 3/2009 | Schieber et al. |
| 2009/0082863 A1 | 3/2009 | Schieber et al. |
| 2009/0132040 A1 | 5/2009 | Frion et al. |
| 2009/0227934 A1 | 9/2009 | Euteneuer et al. |
| 2009/0247955 A1 | 10/2009 | Yamamoto et al. |
| 2009/0287143 A1 | 11/2009 | Line |
| 2009/0287233 A1 | 11/2009 | Huculak |
| 2010/0019177 A1 | 1/2010 | Luckevich |
| 2010/0087774 A1 | 4/2010 | Haffner et al. |
| 2010/0121248 A1 | 5/2010 | Yu et al. |
| 2010/0121342 A1 | 5/2010 | Schieber et al. |
| 2010/0173866 A1 | 7/2010 | Hee et al. |
| 2010/0179652 A1 | 7/2010 | Yamamoto et al. |
| 2010/0222802 A1 | 9/2010 | Gillespie |
| 2010/0241046 A1 | 9/2010 | Pinchuk et al. |
| 2010/0262174 A1 | 10/2010 | Sretavan et al. |
| 2011/0009874 A1 | 1/2011 | Wardle et al. |
| 2011/0009958 A1 | 1/2011 | Wardle et al. |
| 2011/0098809 A1 | 4/2011 | Wardle et al. |
| 2011/0224597 A1 | 9/2011 | Stegmann et al. |
| 2011/0238009 A1 | 9/2011 | Meron et al. |
| 2011/0238075 A1 | 9/2011 | Clauson et al. |
| 2011/0306915 A1 | 12/2011 | De Juan, Jr. et al. |
| 2012/0010702 A1 | 1/2012 | Stegmann et al. |
| 2012/0123315 A1 | 5/2012 | Horvath et al. |
| 2012/0123434 A1 | 5/2012 | Grabner et al. |
| 2012/0136306 A1 | 5/2012 | Bartha |
| 2012/0165720 A1 | 6/2012 | Horvath et al. |
| 2012/0191064 A1 | 7/2012 | Conston et al. |
| 2012/0197175 A1 | 8/2012 | Horvath et al. |
| 2012/0203160 A1 | 8/2012 | Kahook et al. |
| 2012/0220917 A1 | 8/2012 | Silvestrini et al. |
| 2012/0310072 A1 | 12/2012 | Grieshaber |
| 2012/0310137 A1 | 12/2012 | Silvestrini |
| 2012/0325704 A1 | 12/2012 | Kerns et al. |
| 2013/0041346 A1 | 2/2013 | Alon |
| 2013/0150959 A1 | 6/2013 | Schieber et al. |
| 2013/0158462 A1 | 6/2013 | Wardle et al. |
| 2013/0245600 A1 | 9/2013 | Yamamoto et al. |
| 2013/0274655 A1 | 10/2013 | Jennings et al. |
| 2014/0018771 A1 | 1/2014 | Shekalim |
| 2014/0066833 A1 | 3/2014 | Yaron et al. |
| 2014/0081194 A1 | 3/2014 | Burns et al. |
| 2014/0121584 A1 | 5/2014 | Wardle et al. |
| 2014/0128847 A1 | 5/2014 | Lopez |
| 2014/0135916 A1 | 5/2014 | Clauson et al. |

(56) References Cited

U.S. PATENT DOCUMENTS

| | | |
|---|---|---|
| 2014/0163448 A1 | 6/2014 | Lind et al. |
| 2014/0171852 A1 | 6/2014 | Khor |
| 2014/0194916 A1 | 7/2014 | Ichikawa |
| 2014/0213958 A1 | 7/2014 | Clauson et al. |
| 2014/0236066 A1 | 8/2014 | Horvath et al. |
| 2014/0276332 A1 | 9/2014 | Crimaldi et al. |
| 2014/0288485 A1 | 9/2014 | Berlin |
| 2014/0309599 A1 | 10/2014 | Schaller |
| 2014/0364791 A1 | 12/2014 | Stegmann et al. |
| 2015/0005623 A1 | 1/2015 | Grover et al. |
| 2015/0011926 A1 | 1/2015 | Reitsamer et al. |
| 2015/0051699 A1 | 2/2015 | Badawi et al. |
| 2015/0065940 A1 | 3/2015 | Rangel-Friedman et al. |
| 2015/0080783 A1 | 3/2015 | Berlin |
| 2015/0112372 A1 | 4/2015 | Perez Grossmann |
| 2015/0119787 A1 | 4/2015 | Wardle et al. |
| 2015/0125328 A1 | 5/2015 | Bourne et al. |
| 2015/0133946 A1 | 5/2015 | Horvath et al. |
| 2015/0148615 A1 | 5/2015 | Brennan et al. |
| 2015/0216729 A1 | 8/2015 | Doci |
| 2015/0223981 A1 | 8/2015 | Smedley et al. |
| 2015/0223983 A1 | 8/2015 | Schieber et al. |
| 2015/0223984 A1 | 8/2015 | Schieber et al. |
| 2015/0250649 A1 | 9/2015 | Euteneuer et al. |
| 2015/0257932 A1 | 9/2015 | Pinchuk et al. |
| 2015/0282982 A1 | 10/2015 | Schieber et al. |
| 2015/0313758 A1 | 11/2015 | Wilcox |
| 2015/0320596 A1 | 11/2015 | Gifford, III et al. |
| 2015/0374545 A1 | 12/2015 | Horvath et al. |
| 2016/0022486 A1 | 1/2016 | Clauson et al. |
| 2016/0051408 A1 | 2/2016 | Baerveldt et al. |
| 2016/0095985 A1 | 4/2016 | Novak |
| 2016/0100980 A1 | 4/2016 | Badawi et al. |
| 2016/0106589 A1 | 4/2016 | Mittelstein et al. |
| 2016/0135994 A1 | 5/2016 | Romoda et al. |
| 2016/0143778 A1 | 5/2016 | Aljuri et al. |
| 2016/0151204 A1 | 6/2016 | Haffner et al. |
| 2016/0158453 A1 | 6/2016 | Oakley et al. |
| 2016/0220417 A1 | 8/2016 | Schieber et al. |
| 2016/0220418 A1 | 8/2016 | Sorensen et al. |
| 2016/0256317 A1 | 9/2016 | Horvath et al. |
| 2016/0256323 A1 | 9/2016 | Horvath et al. |
| 2016/0287438 A1 | 10/2016 | Badawi et al. |
| 2016/0302965 A1 | 10/2016 | Erickson et al. |
| 2016/0331588 A1 | 11/2016 | Ambati et al. |
| 2016/0346006 A1 | 12/2016 | Hickengbotham et al. |
| 2016/0354248 A1 | 12/2016 | Kahook |
| 2017/0202707 A1 | 7/2017 | Badawi et al. |
| 2017/0258507 A1 | 9/2017 | Hetherington |
| 2018/0243131 A1 | 8/2018 | Erickson et al. |
| 2018/0263817 A1 | 9/2018 | Roeber et al. |
| 2018/0271699 A1 | 9/2018 | Badawi et al. |
| 2019/0142632 A1 | 5/2019 | Badawi et al. |
| 2019/0314200 A1 | 10/2019 | Badawi et al. |
| 2020/0038243 A1 | 2/2020 | Badawi et al. |
| 2020/0129333 A1 | 4/2020 | Badawi et al. |
| 2021/0236333 A1 | 8/2021 | Badawi et al. |
| 2021/0386584 A1 | 12/2021 | Badawi et al. |
| 2022/0104967 A1 | 4/2022 | Badawi et al. |
| 2022/0168146 A1 | 6/2022 | Badawi et al. |
| 2022/0280339 A1 | 9/2022 | Badawi et al. |
| 2022/0280340 A1 | 9/2022 | Badawi et al. |
| 2022/0354695 A1 | 11/2022 | Badawi et al. |
| 2022/0378612 A1 | 12/2022 | Badawi et al. |
| 2023/0181355 A1 | 6/2023 | Badawi et al. |
| 2023/0233371 A1 | 7/2023 | Badawi et al. |
| 2023/0233372 A1 | 7/2023 | Badawi et al. |

FOREIGN PATENT DOCUMENTS

| | | |
|---|---|---|
| CN | 1678407 A | 10/2005 |
| CN | 101505830 A | 8/2009 |
| CN | 201824103 U | 5/2011 |
| CN | 102202706 A | 9/2011 |
| CN | 202400240 U | 8/2012 |
| EP | 2 830 553 B1 | 12/2017 |
| JP | 03-168154 A | 7/1991 |
| JP | 2002-541976 A | 12/2002 |
| JP | 2003-180730 A | 7/2003 |
| JP | 2005-510317 A | 4/2005 |
| JP | 2005-538809 A | 12/2005 |
| JP | 2007-527251 A | 9/2007 |
| JP | 2012-527318 A | 11/2012 |
| JP | 2013-512707 A | 4/2013 |
| JP | 2014-036867 A | 2/2014 |
| JP | 2014-533600 A | 12/2014 |
| WO | WO-00/64391 A1 | 11/2000 |
| WO | WO-00/64393 A1 | 11/2000 |
| WO | WO-01/97727 A1 | 12/2001 |
| WO | WO-02/36052 A1 | 5/2002 |
| WO | WO-03/045582 A1 | 6/2003 |
| WO | WO-2004/026361 A1 | 4/2004 |
| WO | WO-2004/069664 A2 | 8/2004 |
| WO | WO-2005016418 A1 * | 2/2005 ......... A61F 9/00781 |
| WO | WO-2005/105197 A2 | 11/2005 |
| WO | WO-2005/107664 A2 | 11/2005 |
| WO | WO-2005/117752 A1 | 12/2005 |
| WO | WO-2006/066103 A2 | 6/2006 |
| WO | WO-2008/002377 A1 | 1/2008 |
| WO | WO-2009/042596 A2 | 4/2009 |
| WO | WO-2009/067369 A1 | 5/2009 |
| WO | WO-2009/111645 A1 | 9/2009 |
| WO | WO-2010/065970 A1 | 6/2010 |
| WO | WO-2011/006078 A1 | 1/2011 |
| WO | WO-2011/006113 A1 | 1/2011 |
| WO | WO-2011/050360 A1 | 4/2011 |
| WO | WO-2011/097408 A1 | 8/2011 |
| WO | WO-2011/106781 A1 | 9/2011 |
| WO | WO-2013/141898 A1 | 9/2013 |
| WO | WO-2016/042162 A1 | 3/2016 |
| WO | WO-2016/159999 A1 | 10/2016 |

OTHER PUBLICATIONS

Corrected Notice of Allowability dated Nov. 23, 2018, for U.S. Appl. No. 14/816,822, filed Aug. 3, 2015, 2 pages.
Corrected Notice of Allowability dated Dec. 12, 2018, for U.S. Appl. No. 14/816,822, filed Aug. 3, 2015, 2 pages.
Corrected Notice of Allowability dated Feb. 21, 2019, for U.S. Appl. No. 14/675,580, filed Mar. 31, 2015, 6 pages.
Corrected Notice of Allowability dated Apr. 3, 2019, for U.S. Appl. No. 14/675,580, filed Mar. 31, 2015, 3 pages.
Extended European Search Report dated Apr. 22, 2015, for EP Patent Application No. 11 740 372.5, filed Feb. 3, 2011, six pages.
Extended European Search Report dated Jun. 9, 2016, for European Patent Application No. 16 155 079.3, filed on May 31, 2007, 7 pages.
Extended European Search Report dated May 17, 2011, for European Patent Application No. 11 162 487.0, filed on May 31, 2007, 6 pages.
Extended European Search Report dated Mar. 24, 2016, for European Patent Application No. 12 871 982.0, filed on Oct. 4, 2012, 7 pages.
Extended European Search Report dated Nov. 20, 2018, for European Patent Application No. 15 888 007.0, filed on Mar. 31, 2015, 9 pages.
Final Office Action dated Nov. 1, 2010, for U.S. Appl. No. 11/475,523, filed Jun. 26, 2006, 12 pages.
Final Office Action dated Jul. 19, 2012, for U.S. Appl. No. 13/245,811, filed Sep. 26, 2011, 6 pages.
Final Office Action dated Feb. 1, 2013, for U.S. Appl. No. 13/020,706, filed Feb. 3, 2011, 6 pages.
Final Office Action dated Sep. 15, 2014, for U.S. Appl. No. 13/025,112, filed Feb. 10, 2011, 13 pages.
Final Office Action dated Sep. 20, 2013, for U.S. Appl. No. 13/644,780, filed Oct. 4, 2012, 16 pages.
Final Office Action dated Nov. 12, 2013, for U.S. Appl. No. 13/644,748, filed Oct. 4, 2012, 8 pages.
Final Office Action dated Jan. 8, 2014, for U.S. Appl. No. 13/644,758, filed Oct. 4, 2012, 8 pages.

(56) References Cited

OTHER PUBLICATIONS

Final Office Action dated Sep. 3, 2014, for U.S. Appl. No. 13/644,758, filed Oct. 4, 2012, 8 pages.
Final Office Action dated Apr. 23, 2015, for U.S. Appl. No. 14/527,292, filed Oct. 29, 2014, 8 pages.
Final Office Action dated Aug. 19, 2015, for U.S. Appl. No. 13/445,816, filed Apr. 12, 2012, 6 pages.
Final Office Action dated Mar. 9, 2016, for U.S. Appl. No. 14/539,648, filed Nov. 12, 2014, 11 pages.
Final Office Action dated Oct. 3, 2016, for U.S. Appl. No. 13/644,769, filed Oct. 4, 2012, 27 pages.
Final Office Action dated May 18, 2017, for U.S. Appl. No. 14/539,648, filed Nov. 12, 2014, 14 pages.
Final Office Action dated Jan. 29, 2018, for U.S. Appl. No. 14/973,620, filed Dec. 17, 2015, 19 pages.
Final Office Action dated Apr. 6, 2018, for U.S. Appl. No. 15/683,652, filed Aug. 22, 2017, 11 pages.
Final Office Action dated Jun. 1, 2018, for U.S. Appl. No. 14/816,822, filed Aug. 3, 2015, 6 pages.
Final Office Action dated Oct. 19, 2018, for U.S. Appl. No. 15/683,652, filed Aug. 22, 2017, 8 pages.
Final Office Action dated Apr. 19, 2019, for U.S. Appl. No. 14/973,620, filed Dec. 17, 2015, 12 pages.
International Search Report dated Nov. 30, 2007, for PCT Application No. PCT/US2007/013038, filed on May 31, 2007, 4 pages.
International Search Report dated Apr. 5, 2011, for PCT Application No. PCT/US2011/023643, filed on Feb. 3, 2011, 2 pages.
International Search Report dated Feb. 1, 2013 for PCT Application No. PCT/US2012/058751, filed on Oct. 4, 2012, 4 pages.
International Search Report dated Sep. 14, 2015, for PCT Application No. PCT/US2015/023720, filed on Mar. 31, 2015, 5 pages.
Non-Final Office Action dated May 17, 2010, for U.S. Appl. No. 11/475,523, filed Jun. 26, 2006, 10 pages.
Non-Final Office Action dated Jan. 26, 2012, for U.S. Appl. No. 12/695,053, filed Jan. 27, 2010, 10 pages.
Non-Final Office Action dated Mar. 15, 2012, for U.S. Appl. No. 13/245,811, filed Sep. 26, 2011, 4 pages.
Non-Final Office Action dated May 11, 2012, for U.S. Appl. No. 13/020,706, filed Feb. 3, 2011, 5 pages.
Non-Final Office Action dated Nov. 9, 2012, for U.S. Appl. No. 13/245,811, filed Sep. 26, 2011, 5 pages.
Non-Final Office Action dated Apr. 24, 2013, for U.S. Appl. No. 13/644,780, filed Oct. 4, 2012, 13 pages.
Non-Final Office Action dated Jun. 12, 2013, for U.S. Appl. No. 13/644,748, filed Oct. 4, 2012, 8 pages.
Non-Final Office Action dated Sep. 9, 2013, for U.S. Appl. No. 13/644,758, filed Oct. 4, 2012, 7 pages.
Non-Final Office Action dated Feb. 7, 2014, for U.S. Appl. No. 13/644,780, filed Oct. 4, 2012, 12 pages.
Non-Final Office Action dated Feb. 24, 2014, for U.S. Appl. No. 13/025,112, filed Feb. 10, 2011, 12 pages.
Non-Final Office Action dated May 15, 2014, for U.S. Appl. No. 13/644,758, filed Oct. 4, 2012, 7 pages.
Non-Final Office Action dated Nov. 28, 2014, for U.S. Appl. No. 13/644,748, filed Oct. 4, 2012, 7 pages.
Non-Final Office Action dated Jan. 14, 2015, for U.S. Appl. No. 13/644,758, filed Oct. 4, 2012, 10 pages.
Non-Final Office Action dated Feb. 4, 2015, for U.S. Appl. No. 13/445,816, filed Apr. 12, 2012, 6 pages.
Non-Final Office Action dated Feb. 23, 2015, for U.S. Appl. No. 13/025,112, filed Feb. 10, 2011, 17 pages.
Non-Final Office Action dated Jul. 10, 2015, for U.S. Appl. No. 13/025,112, filed Feb. 10, 2011, 16 pages.
Non-Final Office Action dated Oct. 7, 2015, for U.S. Appl. No. 14/527,292, filed Oct. 29, 2014, 5 pages.
Non-Final Office Action dated Nov. 3, 2015, for U.S. Appl. No. 14/539,648, filed Nov. 12, 2014, 7 pages.
Non-Final Office Action dated Dec. 14, 2015, for U.S. Appl. No. 13/445,816, filed Apr. 12, 2012, 7 pages.
Non-Final Office Action dated Jun. 7, 2016, for U.S. Appl. No. 14/527,292, filed Oct. 29, 2014, 5 pages.
Non-Final Office Action dated Feb. 25, 2016, for U.S. Appl. No. 13/644,769, filed Oct. 4, 2012, 19 pages.
Non-Final Office Action dated Jan. 18, 2017, for U.S. Appl. No. 14/539,648, filed Nov. 12, 2014, 13 pages.
Non-Final Office Action dated Mar. 22, 2017, for U.S. Appl. No. 13/644,769, filed Oct. 4, 2012, 31 pages.
Non-Final Office Action dated Aug. 28, 2017, for U.S. Appl. No. 14/973,620, filed Dec. 17, 2015, 6 pages.
Non-Final Office Action dated Nov. 7, 2017, for U.S. Appl. No. 14/816,822, filed Aug. 3, 2015, 14 pages.
Non-Final Office Action dated Dec. 15, 2017, for U.S. Appl. No. 15/343,147, filed Nov. 3, 2016, 12 pages.
Non-Final Office Action dated Apr. 4, 2018, for U.S. Appl. No. 14/675,580, filed Mar. 31, 2015, 10 pages.
Non-Final Office Action dated Aug. 9, 2018, for U.S. Appl. No. 15/182,165, filed Jun. 14, 2016, 9 pages.
Non-Final Office Action dated Aug. 29, 2018, for U.S. Appl. No. 14/973,620, filed Dec. 17, 2015, 11 pages.
Non-Final Office Action dated Sep. 20, 2018, for U.S. Appl. No. 15/340,911, filed Nov. 1, 2016, 7 pages.
Non-Final Office Action dated Oct. 7, 2019, for U.S. Appl. No. 15/854,126, filed Dec. 26, 2017, 13 pages.
Non-Final Office Action dated Nov. 25, 2019, for U.S. Appl. No. 16/189,882, filed Nov. 13, 2018, 12 pages.
Notice of Allowance dated Feb. 2, 2011, for U.S. Appl. No. 11/475,523, filed Jun. 26, 2006, 6 pages.
Notice of Allowance dated Jun. 11, 2012, for U.S. Appl. No. 12/695,053, filed Jan. 27, 2010, 7 pages.
Notice of Allowance dated Apr. 2, 2013, for U.S. Appl. No. 13/245,811, filed Sep. 26, 2011, 6 pages.
Notice of Allowance dated May 10, 2013, for U.S. Appl. No. 13/020,706, filed Feb. 3, 2011, 8 pages.
Notice of Allowance dated Jul. 7, 2014, for U.S. Appl. No. 14/012,963, filed Aug. 28, 2013, 6 pages.
Notice of Allowance dated Jul. 23, 2014, for U.S. Appl. No. 13/644,780, filed Oct. 4, 2012, 8 pages.
Notice of Allowance dated Mar. 30, 2015, for U.S. Appl. No. 13/644,748, filed Oct. 4, 2012, 5 pages.
Notice of Allowance dated Aug. 10, 2015, for U.S. Appl. No. 13/644,758, filed Oct. 4, 2012, 7 pages.
Notice of Allowance dated Mar. 1, 2016, for U.S. Appl. No. 13/025,112, filed Feb. 10, 2011, 7 pages.
Corrected Notice of Allowability dated Apr. 25, 2016, U.S. Appl. No. 13/025,112, filed Feb. 10, 2011, 2 pages.
Notice of Allowance dated Jul. 13, 2016, for U.S. Appl. No. 13/445,816, filed Apr. 12, 2012, 7 pages.
Corrected Notice of Allowability dated Sep. 1, 2016, for U.S. Appl. No. 13/445,816, filed Apr. 12, 2012, 2 pages.
Notice of Allowance dated Oct. 25, 2017, for U.S. Appl. No. 13/644,769, filed Oct. 4, 2012, 8 pages.
Notice of Allowance dated Nov. 21, 2017, for U.S. Appl. No. 14/539,648, filed Nov. 12, 2014, 10 pages.
Notice of Allowance dated Aug. 31, 2018, for U.S. Appl. No. 14/816,822, filed Aug. 3, 2015, 7 pages.
Notice of Allowance dated Jan. 9, 2019, for U.S. Appl. No. 14/675,580, filed Mar. 31, 2015, 9 pages.
Notice of Allowance dated Feb. 6, 2019, for U.S. Appl. No. 15/182,165, filed Jun. 14, 2016, 8 pages.
Notice of Allowance dated Apr. 15, 2019, for U.S. Appl. No. 15/683,652, filed Aug. 22, 2017, 5 pages.
Notice of Allowance dated Apr. 23, 2019, for U.S. Appl. No. 15/340,911, filed Nov. 1, 2016, 5 pages.
Written Opinion dated Nov. 30, 2007, for PCT Application No. PCT/US2007/013038, filed on May 31, 2007, 6 pages.
Written Opinion dated Apr. 5, 2011, for PCT Application No. PCT/US2011/023643, filed on Feb. 3, 2011, 5 pages.
Written Opinion dated Feb. 1, 2013 for PCT Application No. PCT/US2012/058751, filed on Oct. 4, 2012, 6 pages.
Written Opinion dated Sep. 14, 2015 for PCT Application No. PCT/US15/23720, filed on Mar. 31, 2015, 8 pages.

(56) References Cited

OTHER PUBLICATIONS

Final Office Action dated Jun. 9, 2020, for U.S. Appl. No. 15/854,126, filed Dec. 26, 2017, 9 pages.
Final Office Action dated Jun. 9, 2020, for U.S. Appl. No. 16/189,882, filed Nov. 13, 2018, 12 pages.
Bahler, C.K. et al. (2004). "Trabecular bypass stents decrease intraocular pressure in cultured human anterior segments," Am. J. Ophthalmol. 138:988-994.
Butany, J. et al. (2005). "Coronary artery stents; identification and evaluation," J. Clin. Pathol. 58:795-804.
ClinicalTrials.Gov (2006). A study of the trabecular micro-bypass stent in combnination with cataract surgery in subjects with open angle glaucoma, NCT00323284, 6 total pages.
Colombo, A. et al. (2002). "Selection of coronary stents," J. Am. Coll. Cardiol. 40:1021-1033.
Corrected Notice of Allowability dated Oct. 12, 2021, for U.S. Appl. No. 16/532,260, filed Aug. 5, 2019, 2 pages.
Corrected Notice of Allowability dated Apr. 15, 2022, for U.S. Appl. No. 17/239,270, filed Apr. 23, 2021, 2 pages.
Corrected Notice of Allowability dated Oct. 14, 2022, for U.S. Appl. No. 17/033,408, filed Sep. 25, 2020, 2 pages.
Defendant Ivantis, Inc.'s Corrected Initial Invalidity Contentions, In the United States District Court for the District of Delaware, C.A. No. 21-1317-VAC-SRF, 53 total pages.
Drusedau, M.U.H. et al. (2000). "Viscocanalostomy for primary open-angle glaucoma: The gross Pankow experience," J. Cataract Refract. Surg. 26:1367-1373.
Extended European Search Report dated Feb. 4, 2022, for European Patent Application No. 21 179 625.5, filed on Mar. 31, 2015, 8 pages.
Final Office Action dated Apr. 1, 2021, for U.S. Appl. No. 16/532,260, filed Aug. 5, 2019, 8 pages.
Final Office Action dated Dec. 21, 2021, for U.S. Appl. No. 17/239,270, filed Apr. 23, 2021, 14 pages.
Glaukos iStent (2022). iStent inject® W, 9 total pages.
Guerrero, A.H. et al. (2000). "Complications of glaucoma drainage implant surgery," Int. Ophthalmol. Clin. 40:149-163.
Johnson, D.H. et al. (2001). "How does nonpenetrating glaucoma surgery work? Aqueous outflow resistance and glaucoma surgery." J. Glaucoma 10:55-67.
Minckler, D. et al. (2006). "Aqueous shunts for glaucoma (review," Cochrane Library, 47 total pages.
Non-Final Office Action dated Aug. 10, 2020, for U.S. Appl. No. 14/973,620, filed Dec. 17, 2015, 8 pages.
Non-Final Office Action dated Oct. 1, 2020, for U.S. Appl. No. 16/397,733, filed Apr. 29, 2019, 7 pages.
Non-Final Office Action dated Jul. 15, 2021, for U.S. Appl. No. 17/239,263, filed Apr. 23, 2021, 9 pages.
Non-Final Office Action dated Aug. 26, 2021, for U.S. Appl. No. 17/239,270, filed Apr. 23, 2021, 21 pages.
Non-Final Office Action dated Mar. 4, 2022, for U.S. Appl. No. 17/553,671, filed Dec. 16, 2021, 9 pages.
Non-Final Office Action dated Mar. 10, 2022, for U.S. Appl. No. 17/553,408, filed Dec. 16, 2021, 18 pages.
Non-Final Office Action dated Apr. 26, 2022, for U.S. Appl. No. 16/413,466, filed May 15, 2019, 8 pages.
Non-Final Office Action dated Aug. 4, 2022, for U.S. Appl. No. 17/827,494, filed May 27, 2022, 20 pages.
Non-Final Office Action dated Aug. 24, 2022, for U.S. Appl. No. 17/827,485, filed May 27, 2022, 25 pages.
Notice of Allowance dated Aug. 20, 2020, for U.S. Appl. No. 16/189,882, filed Nov. 13, 2018, 8 pages.
Notice of Allowance dated Sep. 16, 2020, for U.S. Appl. No. 15/854,126, filed Dec. 26, 2017, 9 pages.
Notice of Allowance dated Aug. 2, 2021, for U.S. Appl. No. 17/239,263, filed Apr. 23, 2021, 5 pages.
Notice of Allowance dated Sep. 17, 2021, for U.S. Appl. No. 16/532,260, filed Aug. 5, 2019, 9 pages.
Notice of Allowance dated Mar. 15, 2022, for U.S. Appl. No. 17/239,270, filed Apr. 23, 2021, 8 pages.
Notice of Allowance dated May 31, 2022, for U.S. Appl. No. 17/553,671, filed Dec. 16, 2021, 7 pages.
Notice of Allowance dated Jun. 8, 2022, for U.S. Appl. No. 16/413,466, filed May 15, 2019, 5 pages.
Notice of Allowance dated Jun. 28, 2022, for U.S. Appl. No. 17/553,408, filed Dec. 16, 2021, 9 pages.
Notice of Allowance dated Jul. 8, 2022, for U.S. Appl. No. 17/033,408, filed Sep. 25, 2020, 12 pages.
Samuelson, T.W. (2011). "Randomized evaluation of the trabecular micro-bypass stent with phacoemulsification in patients with glaucoma and cataract," Ophthalmol. 118:459-467.
Schwartz, K.S. et al. (2006). "Glaucoma drainage implants: A critical comparison of types," Curr. Opin. Ophthalmol. 17:181-189.
Sidoti, P.A. et al. (1994). "Glaucoma drainage implants," Curr. Opin. Ophthalmol. 11:85-98.
Stefansson, J. (1925). "American journal of ophthalmology," vol. 8, pp. 681-693.
Yablonski, M.E. (2005). "Trabeculectomy with internal tube shunt—A novel glaucoma surgery," J. Glaucoma 14:91-97.
Zhou, J. et al. (2006). "Trabecular bypass—Effect of Schlemm canal and collector channel dilation," J. Glaucoma 15:446-455.
Ahn, W. et al. (2002). "The "Gauge" System for the Medical Use," Anesth. Analg. 95:1125, with Table 1.
Aragona, P. et al. (2002). "Long Term Treatment with Sodium Hyaluronate-Containing Artificial Tears Reduces Ocular Surface Damage in Patients with Dry Eye," Br. J. Ophthalmol. 86:181-184.
Balazs, E.A. et al. (1972). "Hyaluronic Acid and Replacement of Vitreous and Aqueous Humor," Modern Problems in Ophthalmology 10:3-21.
Jacob, J.S. (1985). "Corneal thickness changes following cataract surgery: effect of lens implantation and sodium hyaluronate," British Journal of Ophthalmology 69:567-571.
Myers, T.D. et al. (1999). "Comparison of the Effects of Viscoelastic Agents on Clinical Properties of the Unfolder Lens Injection System," Journal of Cataract and Refractive Surgery 25:953-958.
Nesterov, A.P. (1970). "Role of Blockage of Schlemm's Canal in Pathogenesis of Primary Open-Angle Glaucoma," Am. J. Ophthalmol. 70:691-696.
Razeghinejad, M.R. et al. (2011). "A History of the Surgical Management of Glaucoma," Optom. Vis. Sci. 88:E39-E47.
Summary of Safety and Effectiveness Data, STAARVISCTM (sodium hyaluronate) Premarket Approval Application (PMA) No. P000046, Apr. 18, 2001, 11 total pages.
Stegmann, R. et al. (1999). "Viscocanalostomy for Open-Angle Glaucoma in Black African Patients," Journal of Cataract & Refractive Surgery 25:316-322.
Stegmann, R. (2002). Robert Stegmann, MD: taking on the challenges of ocular trauma and disease, Ocular Surgery News, located at https://www.healio.com/news/ophthalmology/20120331/robert-stegmann-md-taking-on-the-challenges-of-ocular-trauma-and-disease, 4 total pages.
Wild, G.J. et al. (2001). "Dilation of Schlemm's Canal in Viscocanalostomy: Comparison of 2 Viscoelastic Substances," Journal of Cataract and Refractive Surgery 27:1294-1297.
Alcon-Ivantis Claim Construction Hearing Powerpoint Slides (Feb. 9, 2023). *Sight Sciences, Inc.*, v. *Ivantis, Inc., Alcon Research LLC, Alcon Vision, LLC, and Alcon Inc.*, No. 21-1317-GBW-SRF, 86 total pages.
Final Office Action dated Dec. 27, 2022, for U.S. Appl. No. 17/827,485, filed May 27, 2022, 30 pages.
International Search Report dated Nov. 2, 2022, for PCT Application No. PCT/US2022/031457, filed on May 27, 2022, 4 pages.
Joint Claim Construction Brief (Jan. 26, 2023). *Sight Sciences, Inc.* v. *Ivantis, Inc. Alcon Research LLC, Alcon Vision, LLC and Alcon Inc.*, C.A. No. 21-1317-GBW-SRF, filed on Jan. 26, 2023, In the United States District Court for the District of Delaware, 91 total pages.
Notice of Allowance dated Nov. 23, 2022, for U.S. Appl. No. 17/827,494, filed May 27, 2022, 8 pages.
Petition for Inter Partes Review Under 37 C.F.R. § 42.101 (Sep. 12, 2022). *Ivantis, Inc. Alcon Research LLC, Alcon Vision, LLC and Alcon Inc.*, Petitioners v. *Sight Sciences, Inc.*, Patent Owner, filed on

(56) References Cited

OTHER PUBLICATIONS

Sep. 12, 2022, IPR2022-01529, U.S. Pat. No. 9,370,443, United States Patent and Trademark Office Before the Patent Trial and Appeal Board, 98 total pages.
Petition for Inter Partes Review Under 37 C.F.R. § 42.101 (Sep. 12, 2022). *Ivantis, Inc. Alcon Research LLC, Alcon Vision, LLC and Alcon Inc.*, Petitioners v. *Sight Sciences, Inc.*, Patent Owner, filed on Sep. 12, 2022, IPR2022-01530, U.S. Pat. No. 10,314,742, United States Patent and Trademark Office Before the Patent Trial and Appeal Board, 102 total pages.
Petition for Inter Partes Review Under 37 C.F.R. § 42.101 (Sep. 14, 2022). *Ivantis, Inc. Alcon Research LLC, Alcon Vision, LLC and Alcon Inc.*, Petitioners v. *Sight Sciences, Inc.*, Patent Owner, filed on Sep. 14, 2022, IPR2022-01533, U.S. Pat. No. 8,287,482, United States Patent and Trademark Office Before the Patent Trial and Appeal Board, 107 total pages.
Petition for Inter Partes Review Under 37 C.F.R. § 42.101 (Sep. 16, 2022). *Ivantis, Inc. Alcon Research LLC, Alcon Vision, LLC and Alcon Inc.*, Petitioners v. *Sight Sciences, Inc.*, Patent Owner, filed on Sep. 16, 2022, IPR2022-01540, U.S. Pat. No. 9,486,361, United States Patent and Trademark Office Before the Patent Trial and Appeal Board, 100 total pages.
Second Amended Complaint (Aug. 1, 2022). *Sight Sciences, Inc.* v. *Ivantis, Inc. Alcon Research LLC, Alcon Vision, LLC and Alcon Inc.*, C.A. No. 21-1317-VAC-SRF, filed on Aug. 1, 2022, In the United States District Court for the District of Delaware, 49 total pages.
Second Amended Complaint—Exhibits A-P (Aug. 1, 2022). *Sight Sciences, Inc.* v. *Ivantis, Inc. Alcon Research LLC, Alcon Vision, LLC and Alcon Inc.*, C.A. No. 1-21-1317-GBW-SRF, filed on Aug. 1, 2022, In the United States District Court for the District of Delaware, 345 total pages.
*Sight Sciences, Inc.*, v. *Ivantis, Inc., Alcon Research LLC, Alcon Vision, LLC, and Alcon Inc.*, No. 21- 1317-GBW-SRF (Feb. 9, 2023). Plaintiff's Markman Hearing Presentation, 130 total pages.
Written Opinion of the International Searching Authority dated Nov. 2, 2022, for PCT Application No. PCT/US2022/031457, filed on May 27, 2022, 11 pages.
Abu-Hassan, D.W. et al. (2014). "The trabecular meshwork: A basic review of form and function," J. Ocul. Biol. 2(1), 22 total pages.
Bonsignore, C. (2003). "A decade of evolution in stent design," SMST-2003, Proceedings of the International Conference on Shape and Memory and Superelastic Technologies, pp. 519-528, 13 total pages.
Brubaker, R.F. (2004). "Goldmann's equation and clinical measures of aqueous dynamics," Experimental Eye Research 78:633-637.
Brunette, D.M. et al. (2001). "Chapter 8: Mechanical, thermal, chemical and electrochemical surface treatment of titanium," in Titanium in Medicine: Material science, engineering, biological responses and medical applications, Springer, pp. 232-266.
Corrected Notice of Allowability dated Mar. 3, 2023, for U.S. Appl. No. 17/827,494, filed May 27, 2022, 5 pages.
Defendant Ivantis, Inc.'s Second Supplemental Initial Invalidity Contentions. In the United States District Court for the District of Delaware, Case No. C.A. No. 21-1317-GBW-SRF, filed on Jun. 29, 2023, Sight Sciences, Inc., Plaintiff, with Exhibit Nos. 328 (A17, A18, A19, A20), 361 (A17, A18, A19, A20), 443 (A14, A15, A16, A17), 482 (A14, A15, A16, A17) and 742 (A14, A15, A16, A17, A18), 1,893 total pages.
Dietlein, T.S. et al. (2008). "Combined cataract-glaucoma surgery using the intracanalicular Eyepass glaucoma implant: first clinical results of a prospective pilot study," J. Cataract Refract Surg. 34:247-252.
Duerig, T. et al. (1999). "An overview of nitinol medical applications," Materials Science and Engineering A273-275:149-160.
Food and Drug Administration (Apr. 1, 2004). "Title 21—Food and Drugs Chapter I—Food and Drug Administration Department of Health and Human Services Subchapter H—Medical Devices," 2 total pages.
Glaukos Corporation iStent® Trabecular Micro-Bypass Stent (2021). Directions for Use/Package Insert, 23 total pages.
Healio (May 4, 2004). "EyePass glaucoma device shows promise," Ocular Surgery News, located at https://www.healio.com/news/ophthalmology/20120331/eyepass-glaucoma-device-shows-promise, 2 total pages.
Healio (Sep. 15, 2002). "Robert Stegmann, MD: taking on the challenges of ocular trauma and disease," Ocular Surgery News 20th Anniversary, 5 total pages.
Hill, R. (Nov./Dec. 2012). "Sidebar: Inventor's Perspective," located at https://glaucomatoday.com/articles/2012-nov-dec/sidebar-inventors-perspective, 3 total pages.
Hsu, S.W. et al. (May 2006). "In Vitro Studies of the Neuroform Microstent Using Transparent Human Intracranial Arteries," AJNR Am. J. Neuroradiol. 27:1135-1139.
Khng, C. et al. (2008). "Evaluation of the relationship between corneal diameter and lens diameter," J. Cataract Refract. Surg. 34:475-479.
Llobet, A et al. (2003). "Understanding Trabecular Meshwork Physiology: A Key to the Control of Intraocular Pressure?" News Physiol. Sci. 18:205-209.
Mishra, P et al. (Nov. 17, 2014). "Glaucoma drainage device: A review," Journal of Evolution and Medical and Dental Sciences, vol. 3, Issue 62, pp. 13744-13758.
Nitinol Product Information (2003). Memry Materials, 5 total pages.
Non-Final Office Action dated Mar. 16, 2023, for U.S. Appl. No. 17/397,817, filed Aug. 9, 2021, 8 pages.
Non-Final Office Action dated Jun. 23, 2023, for U.S. Appl. No. 18/130,353, filed Apr. 3, 2023, 15 pages.
Non-Final Office Action dated Jun. 26, 2023, for U.S. Appl. No. 18/130,354, filed Apr. 3, 2023, 16 pages.
Notice of Allowance dated Apr. 27, 2023, for U.S. Appl. No. 17/990,589, filed Nov. 18, 2022, 12 pages.
Notice of Allowance dated May 4, 2023, for U.S. Appl. No. 17/827,485, filed May 27, 2022, 12 pages.
Opening Expert Report of Joseph A. Izatt, Ph.D. In the United States District Court for the District of Delaware, Case No. C.A. No. 21-1317-GBW-SRF, filed on Jul. 11, 2023, Sight Sciences, Inc., Plaintiff, with Exhibit Nos. A and B, 194 total pages.
Opening Expert Report of Angelo P. Tanna, M.D. In the United States District Court for the District of Delaware, Case No. C.A. No. 21-1317-GBW-SRF, filed on Jul. 13, 2023, Sight Sciences, Inc., Plaintiff, with Exhibit Nos. 1 through 22, 936 total pages.
Pride, G.L. et al. (2004). "Stent-coil treatment of a distal internal carotid artery dissecting pseudoaneurysm on a redundant loop by use of a flexible, dedicated nitinol intracranial stent," AJNR Am. J. Neuroradiol. 25:333-337.
Prielipp, R.C. et al. (2007). "Stents, Stents, Everywhere—Now even in the BRAIN," apsf Newsletter, 8 total pages.
Schlemm's Canal Position Inside the Eye (IMAGE), EurekAlert! 2023, located at https://www.eurekalert.org/multimedia/757562, 2 total pages.
Sherwood, M. et al. (Mar. 1, 2006). "Rethinking glaucoma surgery: Aqueous within the eyewall," David E.I. Pyott Glaucoma Education Center, located at https://www.aao.org/education/current-insight/rethinking-glaucoma-surgery-aqueous-within-eyewall, 5 total pages.
Shrestha, S. et al. (2020). "Coronary artery stents: From the beginning to the present," Consultant 60:e1, 13 total pages.
Stoeckel, D. et al. (2002). "A survey of stent designs," Min. Invas. Ther. & Allied Technol. 11:137-147.
Usui, T. et al. (Aug. 2011). "Identification of Schlemm's canal and its surrounding tissues by anterior segment fourier domain optical coherence tomography," Invest. Ophthalmol. Vis. Sci. 52:6934-6939.
Weinreb, R.N. et al. (2004). "Primary open-angle glaucoma," Lancet 363:1711-1720.
Wittman, B. et al. (2017). "Eyepass Glaucoma Implant in Open-Angle Glaucoma After Failed Conventional Medical Therapy: Clinical Results of a 5-Year-Follow-up," J. Glaucoma 26:328-334.

\* cited by examiner

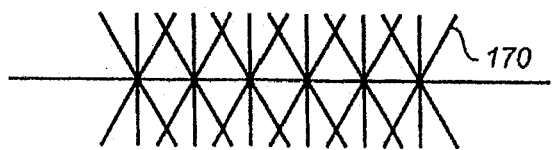
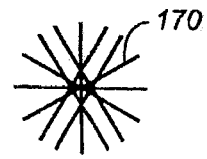
FIG. 8A      FIG. 8B
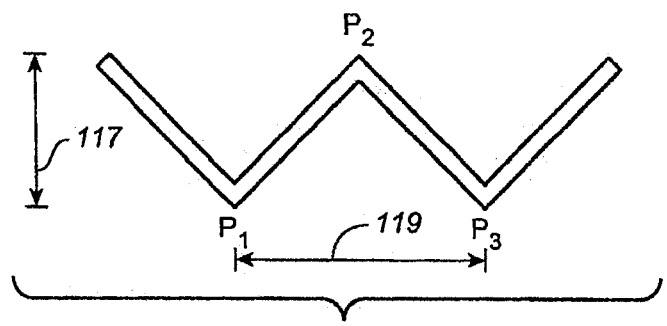
FIG. 8C      FIG. 8D
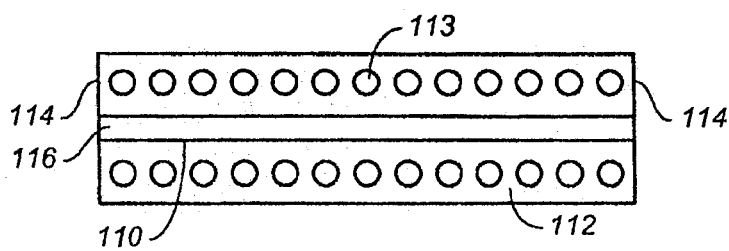
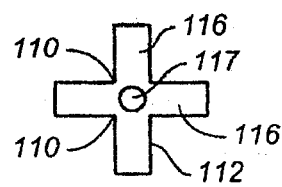
FIG. 8E      FIG. 8F
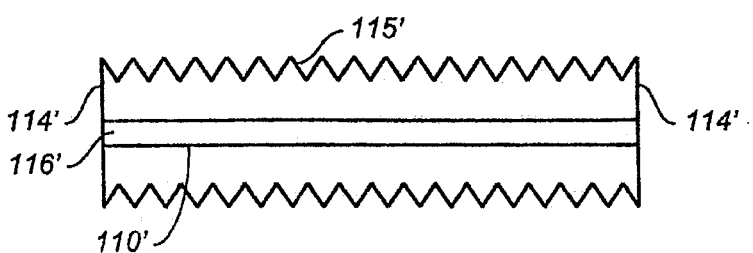
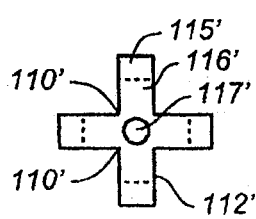
FIG. 8G      FIG. 8H

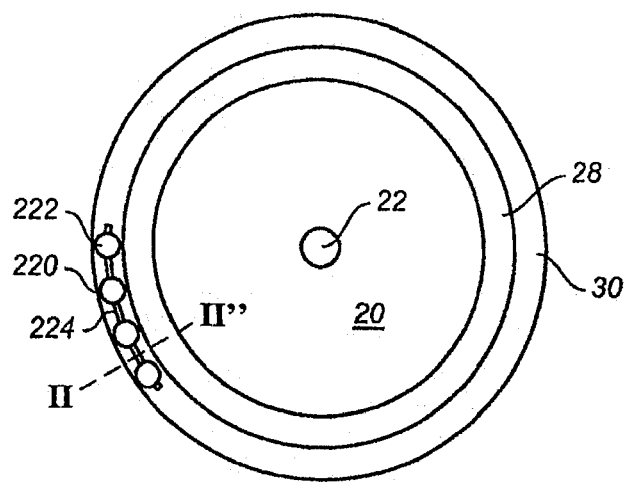
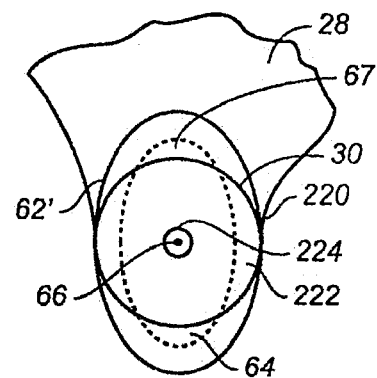
FIG. 12A  FIG. 12B
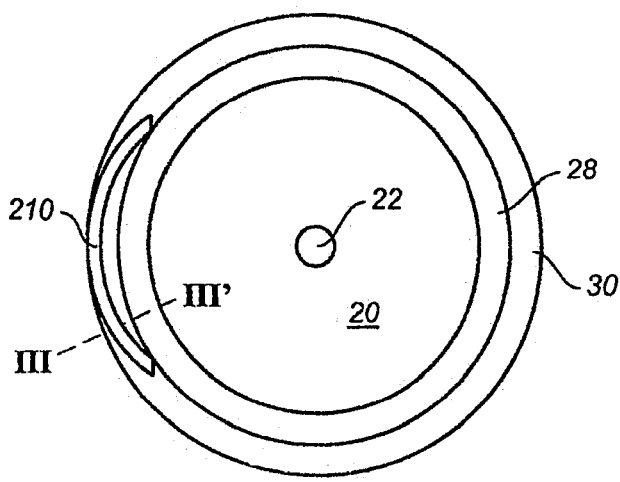
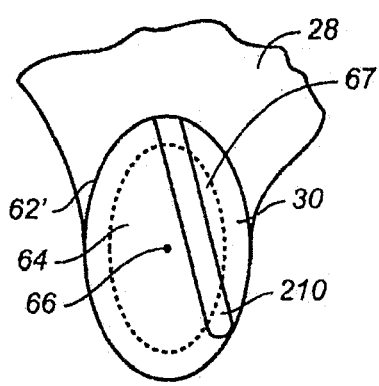
FIG. 12C  FIG. 12D

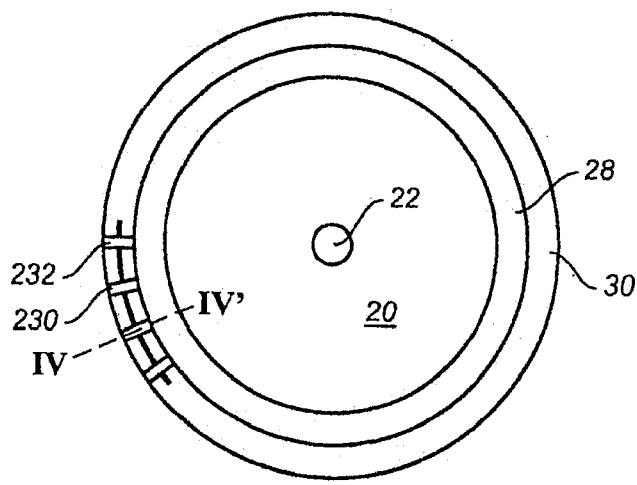
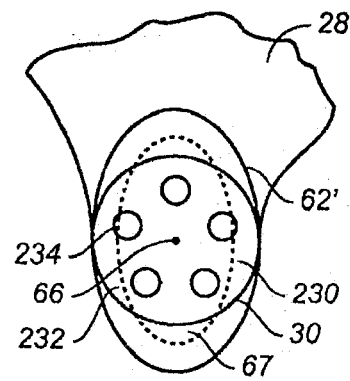
FIG. 12E  FIG. 12F
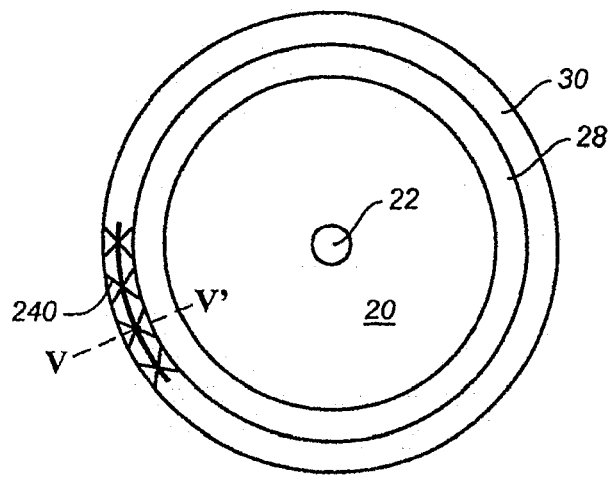
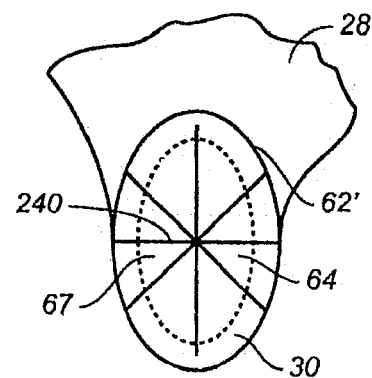
FIG. 12G  FIG. 12H

INTRAOCULAR IMPLANTS AND METHODS AND KITS THEREFOR

CROSS-REFERENCE TO RELATED APPLICATIONS

This application is a continuation of U.S. patent application Ser. No. 15/340,911, filed on Nov. 1, 2016, which is a continuation of U.S. patent application Ser. No. 13/445,816, filed on Apr. 12, 2012 (now U.S. Pat. No. 9,486,361), which is a continuation of U.S. patent application Ser. No. 12/695,053, filed on Jan. 27, 2010 (now U.S. Pat. No. 8,287,482), which is a continuation of U.S. patent application Ser. No. 11/475,523, filed on Jun. 26, 2006 (now U.S. Pat. No. 7,909,789), the disclosures of which are hereby incorporated by reference in their entirety.

FIELD

The devices, kits and methods described herein relate generally to intraocular pressure reduction. More particularly, the devices, kits and methods relate to intraocular implants implantable into Schlemm's canal that can reduce intraocular pressure without substantially interfering with fluid flow across Schlemm's canal.

BACKGROUND

Glaucoma is a potentially blinding disease that affects over 60 million people worldwide, or about 1-2% of the population. Typically, glaucoma is characterized by elevated intraocular pressure. Increased pressure in the eye can cause damage to the optic nerve which can lead to loss of vision if left untreated. Consistent reduction of intraocular pressure can slow down or stop progressive loss of vision associated with glaucoma. In addition, patients are often diagnosed with pre-glaucoma and ocular hypertension when they exhibit symptoms likely to lead to glaucoma, such as somewhat elevated intraocular pressure, but do not yet show indications of optic nerve damage. Treatments for glaucoma, pre-glaucoma and ocular hypertension primarily seek to reduce intraocular pressure.

Increased intraocular pressure is caused by sub-optimal efflux or drainage of fluid (aqueous humor) from the eye. Aqueous humor or fluid is a clear, colorless fluid that is continuously replenished in the eye. Aqueous humor is produced by the ciliary body, and then flows out primarily through the eye's trabecular meshwork. The trabecular meshwork extends circumferentially around the eye at the anterior chamber angle, or drainage angle, which is formed at the intersection between the peripheral iris or iris root, the anterior sclera or scleral spur and the peripheral cornea. The trabecular meshwork feeds outwardly into Schlemm's canal, a narrow circumferential passageway generally surrounding the exterior border of the trabecular meshwork. Positioned around and radially extending from Schlemm's canal are aqueous veins or collector channels that receive drained fluid. The net drainage or efflux of aqueous humor can be reduced as a result of decreased facility of outflow, decreased outflow through the trabecular meshwork and canal of Schlemm drainage apparatus, increased episcleral venous pressure, or possibly, increased production of aqueous humor. Flow out of the eye can be restricted by blockages or constriction in the trabecular meshwork and/or Schlemm's canal.

Glaucoma, pre-glaucoma and ocular hypertension currently can be treated by reducing intraocular pressure using one or more modalities, including medication, incisional surgery, laser surgery, cryosurgery, and other forms of surgery. In the United States, medications or medical therapy are typically the first lines of therapy. If medical therapy is not sufficiently effective, more invasive surgical treatments may be used. In other countries, such as those with socialized medical systems or with nationalized health care systems, surgery may be the first line of therapy if it is considered a more cost effective treatment.

A standard incisional surgical procedure to reduce intraocular pressure is trabeculectomy, or filtration surgery. This procedure involves creating a new drainage site for aqueous humor. Instead of naturally draining through the trabecular meshwork, a new drainage pathway is created by removing a portion of sclera and trabecular meshwork at the drainage angle. This creates an opening or passage between the anterior chamber and the subconjunctival space that is drained by conjunctival blood vessels and lymphatics. The new opening may be covered with sclera and/or conjunctiva to create a new reservoir called a bleb into which aqueous humor can drain. However, trabeculectomy carries both long and short term risks. These risks include blockage of the surgically-created opening through scarring or other mechanisms, hypotony or abnormally low intraocular pressure, expulsive hemorrhage, hyphema, intraocular infection or endophthalmitis, shallow anterior chamber angle, and others. Alternatives to trabeculectomy are actively being sought.

Bypass stents are also used to bridge a blocked trabecular meshwork. Stents can be inserted between the anterior chamber of the eye and Schlemm's canal, bypassing the trabecular meshwork. However, it is difficult to consistently and reliably implant a bypass stent from the anterior chamber into Schlemm's canal. The implant procedure is challenging and stents can become clogged and lose functionality over time. Others have inserted tubular elongated cylindrical hollow stents longitudinally into Schlemm's canal. Cylindrical hollow stents can be configured to allow circumferential fluid flow around the canal. These too can lose functionality over time as a result of occlusion or scarring.

Schlemm's canal is small, approximately 190-370 microns in cross-sectional diameter, and circular. Therefore, it can be difficult or expensive to design and manufacture hollow tubular stents of appropriate dimensions for use in opening Schlemm's canal. In addition, hollow tubular stents can be prone to failure and collapse or occlusion over time, as has been shown for cardiovascular stents. Hollow tubular stents incorporating thin walls are especially prone to failure. Further, the walls of tubular stents placed lengthwise along Schlemm's canal can have significant surface area contact with the trabecular meshwork and/or the collector channels, which can result in blockage of the meshwork or collector channels, substantially interfering with transmural flow across Schlemm's canal and into the eye's collector channels.

Therefore, easily manufacturable, minimally invasive devices for effective, long-term reduction in intraocular pressure are desirable. In addition, methods and kits incorporating such devices are desirable.

SUMMARY

Described here are devices, kits and methods for reducing intraocular pressure. The devices for reducing pressure within the eye comprise a support implantable circumferentially within Schlemm's canal that is configured to maintain the patency of at least a portion of the canal. The support occupies at least a portion of a central core of Schlemm's canal. The support does not substantially interfere with transmural flow across Schlemm's canal, and thereby utilizes the eye's natural drainage pathways. The support can be implanted into Schlemm's canal with minimal trauma to the eye.

The support generally comprises a biocompatible material. At least a portion of the support can be made from a biocompatible polymer, e.g., acrylics, silicones, polymethylmethacrylate, or a hydrogel. In addition, at least part of the support can be made from a biocompatible metal such as gold. In some variations, at least a portion of the support is made from a shape memory material. Suitable shape memory materials include shape memory polymers or shape memory alloys, such as nickel titanium alloys. If a shape memory material is used, the support can have a compressed state prior to and during implantation into Schlemm's canal, and an expanded state following implantation to open the canal.

In some variations, the support is at least partially made from a biocompatible, biodegradable polymer. The biodegradable polymer can be collagen, a collagen derivative, a poly(lactide); a poly(glycolide); a poly(lactide-co-glycolide); a poly(lactic acid); a poly(glycolic acid); a poly(lactic acid-co-glycolic acid); a poly(lactide)/poly(ethylene glycol) copolymer; a poly(glycolide)/poly(ethylene glycol) copolymer; a poly(lactide-co-glycolide)/poly(ethylene glycol) copolymer; a poly(lactic acid)/poly(ethylene glycol) copolymer; a poly(glycolic acid)/poly(ethylene glycol) copolymer; a poly(lactic acid-co-glycolic acid)/poly(ethylene glycol) copolymer; a poly(caprolactone); a poly(caprolactone)/poly(ethylene glycol) copolymer; a polyorthoester; a poly(phosphazene); a poly(hydroxybutyrate) or a copolymer including a poly(hydroxybutyrate); a poly(lactide-co-caprolactone); a polycarbonate; a poly(esteramide); a polyanhydride; a poly(dioxanone); a poly(alkylene alkylate); a copolymer of polyethylene glycol and a polyorthoester; a biodegradable polyurethane; a poly(amino acid); a polyetherester; a polyacetal; a polycyanoacrylate; a poly(oxyethylene)/poly(oxypropylene) copolymer; and blends and copolymers thereof.

The support can comprise an active agent. For example, a support can be coated or impregnated with an active agent. Alternatively, an active agent can be dispersed within the support, e.g., by filling a cavity within the support. The active agent can include a prostaglandin, a prostaglandin analog, a beta blocker, an alpha-2 agonist, a calcium channel blocker, a carbonic anhydrase inhibitor, a growth factor, an anti-metabolite, a chemotherapeutic agent, a steroid, an antagonist of a growth factor, or combinations thereof. The release of the active agent can be controlled using a time release system, e.g., by embedding or encapsulating the active agent with a time release composition.

In some variations, the support will be solid. In other variations, at least a portion of the support will be hollow or porous. The surface of the support may be smooth, rough, spiked, or fluted. In still other variations, at least part of the support will be made from mesh. The support can include at least one fenestration and one or more rod-like members.

In some variations, the support comprises at least two adjacent beads. Adjacent beads can have the same or different sizes and shapes, and can be made from the same or different materials. The bead shapes can be spherical, spheroid, ovoid, cylindrical, cuboid, cubical, conical, discoid, helical, or segments thereof. In some variations, there is a connector linking at least two adjacent beads together. If there is a connector, it can be rigid or flexible. If there is more than one connector, e.g., two connectors inserted between three beads, the connectors may be of the same or different lengths. The connectors can include the same or different material as the beads they connect. A connector can also function as a spacer configured to provide space between adjacent beads. In some variations, the support comprises at least two discs separated by, and connected with, a connector. The discs may include fenestrations. The connector may also comprise a guide wire over which a fenestrated bead can be threaded into the canal of Schlemm.

The support can extend approximately all the way around Schlemm's canal, if the support has a circumference approximately equal to the circumference of Schlemm's canal. Alternatively, the support can extend only about half way around the circumference of Schlemm's canal, or about a quarter way around the canal. In some variations, the support will extend less than a quarter circumference of Schlemm's canal. The support can be configured to contact the inner surface of the wall of Schlemm's canal at two, three or more points. In some variations, the support can be attached to tissue. The support may comprise a stiff arcuate member having a radius of curvature smaller or larger than that of Schlemm's canal.

In some variations, the support can be altered using electromagnetic radiation. For example, a laser having a wavelength absorbable by at least one localized portion of the support can be used to alter the support. In other variations, electromagnetic radiation can be used to release an active agent from the support. In still other variations, the support can be visually enhanced using fluorescence or phosphorescence emission. For example, the support can comprise a chromophore that fluoresces or phosphoresces upon excitation with a light source. In some variations, the emitted fluorescence or phosphorescence is in the wavelength range of about 300 nm to about 800 nm. In some variations, the support can comprise a chromophore that enhances postoperative monitoring of the support.

Kits for reducing intraocular pressure are also provided. The kits contain a support that can be implanted circumferentially within Schlemm's canal. The support is configured to maintain the patency of at least part of Schlemm's canal. The support occupies at least a portion of a central core of Schlemm's canal and does not substantially interfere with transmural flow across the canal. The kits also contain an introducer for implanting the support within the canal. In some variations, the kits include a positioning device for adjusting the support within the canal. In other variations, kits include instructions. In still other variations, the kits include an active agent. Some kits contain at least two supports. If more than one support is included, the kits can include at least two introducers for delivering the supports. Multiple supports within the same kit can have the same or different shape, size, or composition. Multiple supports within the same kit can be connected together or remain separate. In some variations, kits include a fixation device for attaching a support to tissue. In other variations, kits may include a system for visually enhancing the appearance of the support.

Methods for reducing intraocular pressure are also described. The methods include inserting a support circumferentially within Schlemm's canal. The support is configured to maintain the patency of at least part of the canal. The support occupies at least a portion of a central core of Schlemm's canal, and does not substantially interfere with transmural flow across the canal. In some variations, the methods also include dilating Schlemm's canal prior to insertion of the support. In still other variations, the methods comprise anchoring the support to tissue. The methods can include implanting at least two supports. If more than one support is implanted within a single eye, the multiple supports can be positioned circumferentially adjacent to each other or circumferentially opposed (i.e., positioned about 180° apart) to each other within Schlemm's canal. Multiple supports within one eye can be connected or remain separate. In some variations of the methods, the support is illuminated with a light source to visually enhance the position of the support. In other variations of the methods, the support can be altered using electromagnetic radiation. For example, a laser absorbed by at least one localized portion of the support can be used to alter the support. The alteration can comprise the creation or enlargement of an aperture in the support. If electromagnetic radiation is used to alter a support, the alteration can occur before implantation or after implantation.

BRIEF DESCRIPTION OF THE DRAWINGS

FIGS. 8A-B show side and front views, respectively, of a support having an open network structure. FIGS. 8C-D show side and front views, respectively, of a support having a longitudinal zig-zag configuration that will contact the wall of Schlemm's canal at at least three points (labeled $P_1$, $P_2$, $P_3$). FIGS. 8E-F show side and front views, respectively, of a support having a rod-like member with continuously fluted edges and fenestrations. FIGS. 8G-H show side and front views, respectively, of another variation of a support having a rod-like member with continuously fluted edges.

FIG. 12A illustrates a variation of a support traversing the center of the central core of Schlemm's canal. FIG. 12B shows a cross-sectional view along line II-II'. FIG. 12C illustrates a variation of a support traversing the central core of the canal. FIG. 12D shows a cross-sectional view along line III-III'. FIG. 12E illustrates a variation of a support that occupies the majority of the central core of the canal. FIG. 12F shows a cross-sectional view along line IV-IV'. FIG. 12G illustrates a variation of support having an open network that occupies a portion of the central core of the canal. FIG. 12H shows a cross-sectional view along line V-V'.

DETAILED DESCRIPTION

Described here are devices, kits and methods to reduce intraocular pressure by maintaining or restoring Schlemm's canal so that at least a portion of the canal is patent or unobstructed. The devices, kits and methods operate to keep Schlemm's canal from collapsing while not substantially interfering with the eye's natural drainage mechanism for aqueous humor, in which transmural fluid flow across Schlemm's canal occurs. The devices are implantable in Schlemm's canal with minimal trauma to the eye.

Figure 1:
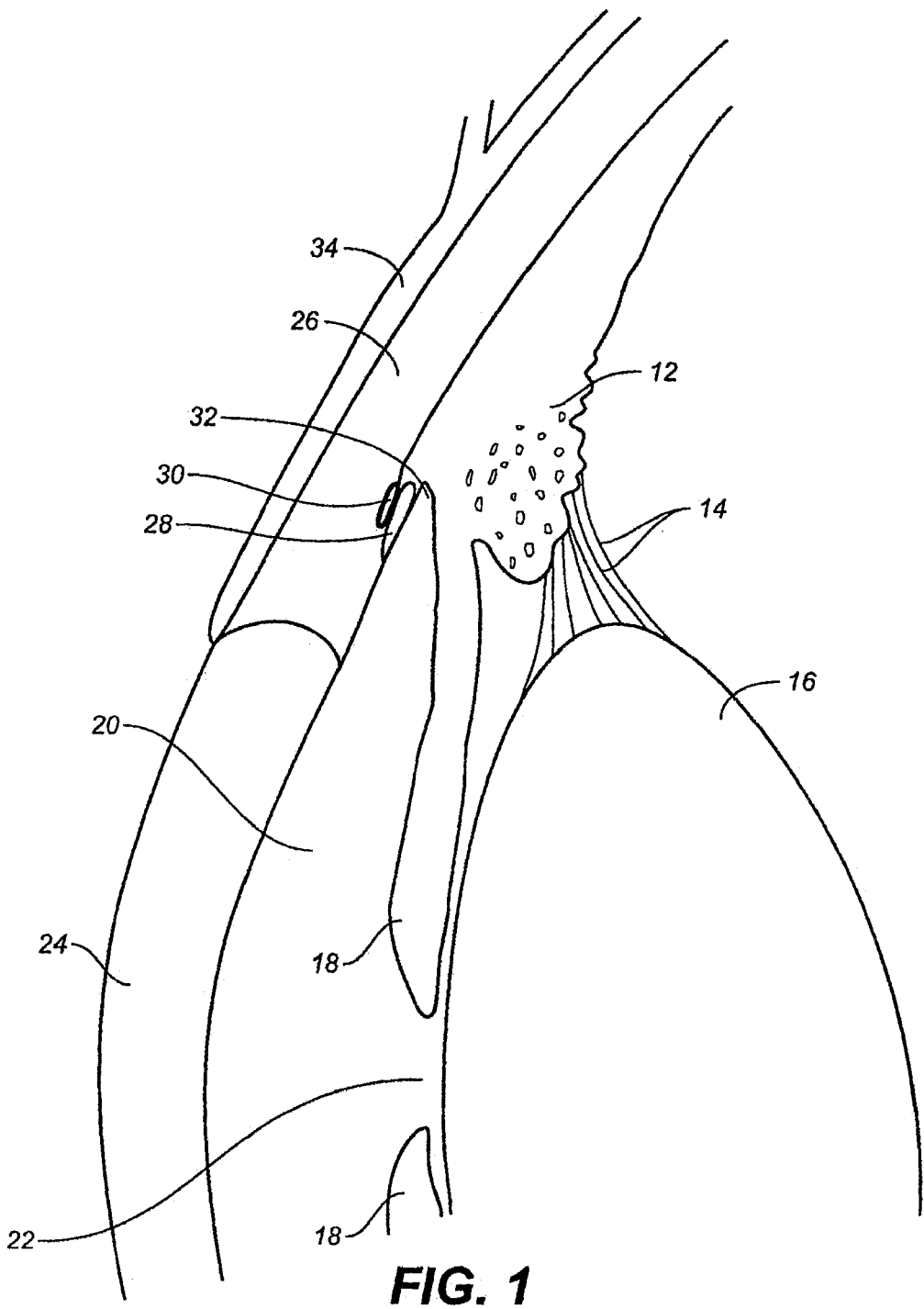
FIG. 1 provides a partial cross-sectional side view of a normal human eye.

With reference to the figures, FIG. 1 shows a partial cross-sectional view of the anatomy of a normal human eye. Ciliary body 12 is connected to iris 18 and to lens 16 via zonular fibrils 14. The anterior chamber of the eye 20 is bounded on its anterior (front) surface by cornea 24. In the center of iris 18 is pupil 22. Cornea 24 is connected on its periphery to sclera 26, which is a tough fibrous tissue forming the white shell of the eye. Trabecular meshwork 28 is located on the outer peripheral surface of anterior chamber 20. The trabecular meshwork extends 360° circumferentially around the anterior chamber. Located on the outer peripheral surface of meshwork 28 is Schlemm's canal 30. Schlemm's canal extends 360° circumferentially around the trabecular meshwork. At the apex formed between iris 18, meshwork 28 and sclera 26 is angle 32. Conjunctiva 34 is a membrane overlaying sclera 26 and lining the inside of the eyelid (not shown).

Figure 2:
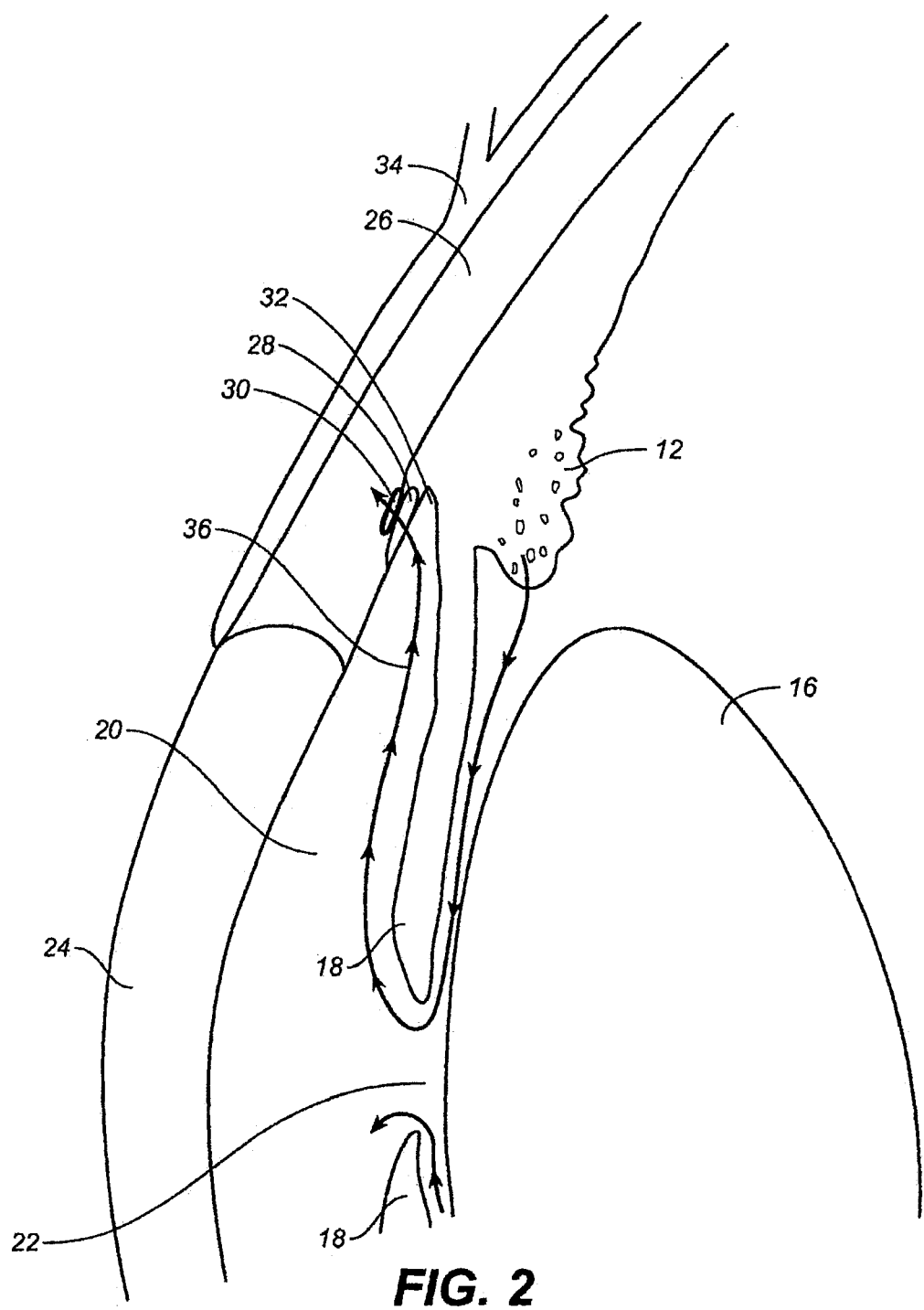
FIG. 2 provides a partial cross-sectional side view of a normal drainage path of fluid from the eye.

FIG. 2 shows a partial cross-sectional view of flow of aqueous humor within and out of a normally functioning human eye. Aqueous humor is produced in ciliary body 12 and its path through and out of the eye is indicated by solid directional line 36. The aqueous humor flows from ciliary body 12, between lens 16 and iris 18, through pupil 22 into anterior chamber 20, across trabecular meshwork 28, across Schlemm's canal 30, into aqueous veins or collector channels (not shown) and finally into the bloodstream via conjunctival vasculature.

Figure 3:
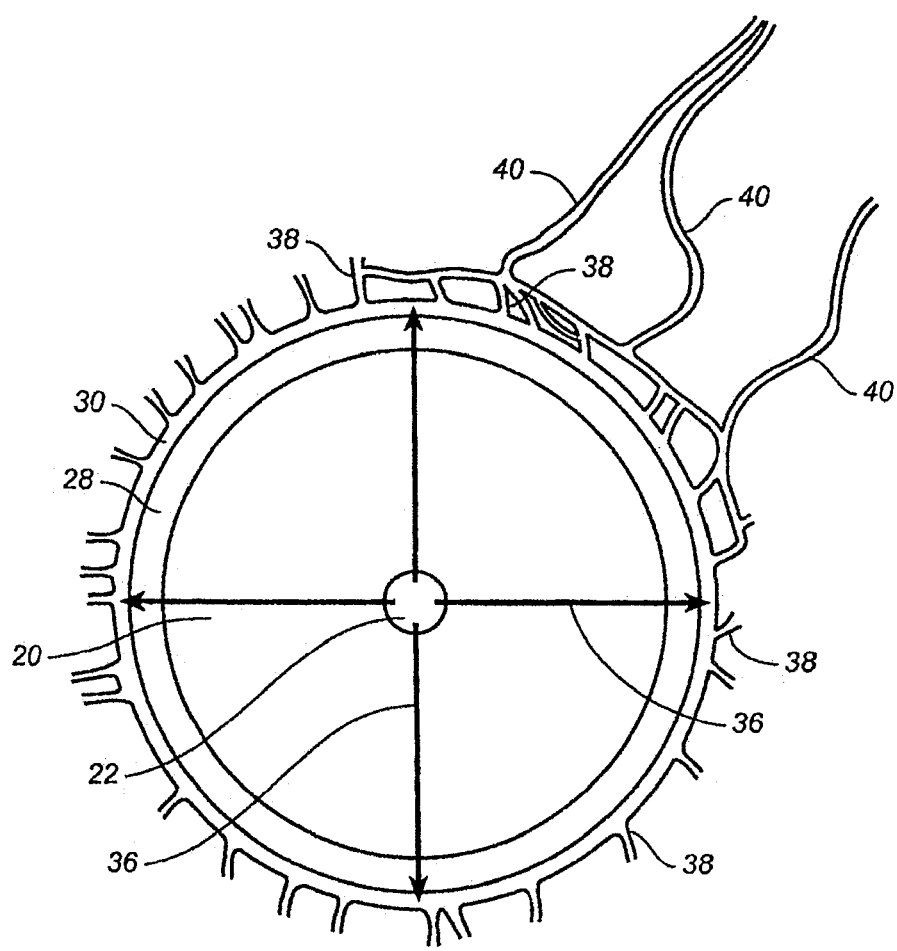
FIG. 3 shows a front view of normal fluid drainage from the eye.

FIG. 3 shows a front view of normal flow of aqueous humor out of the eye. Aqueous humor enters anterior chamber 20 via pupil 22. The fluid flows outwardly toward the periphery of the eye, with the general path of flow indicated by solid directional lines 36. The fluid crosses trabecular meshwork 28 and traverses Schlemm's canal 30 to reach aqueous veins or collector channels 38. There are typically 25-30 collector channels located in a human eye. Collector channels 38 are connected to vasculature 40, whereby the drained aqueous humor enters the bloodstream. Although the direction of net or bulk fluid flow is depicted as radially outward by directional lines 36 from pupil 22 for simplicity, actual fluid flow in an eye may follow more varied paths.

Figure 4A:
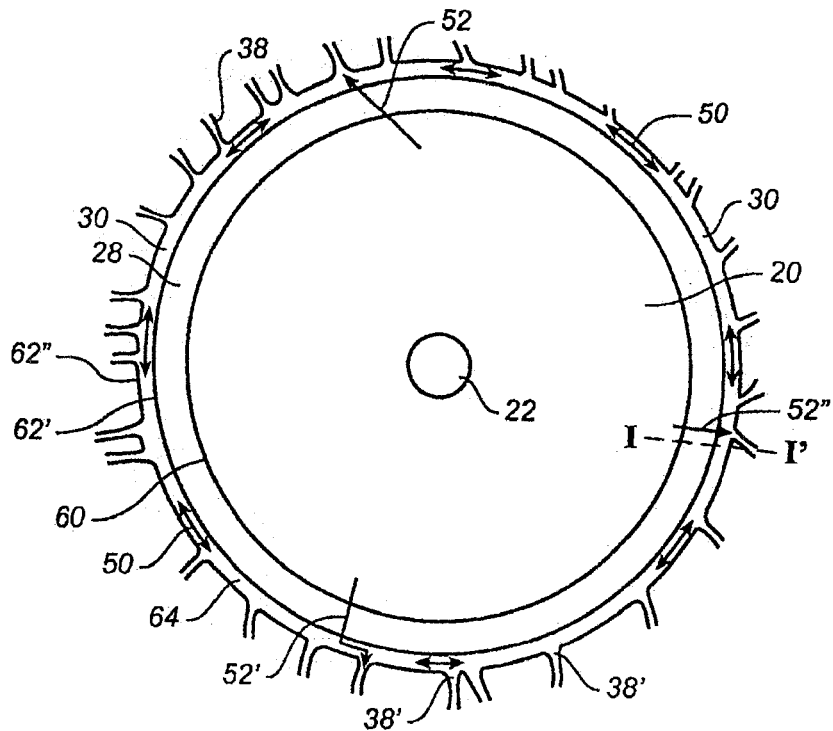
FIG. 4A shows an alternative front view of normal fluid drainage paths from the eye.
Figure 4B:
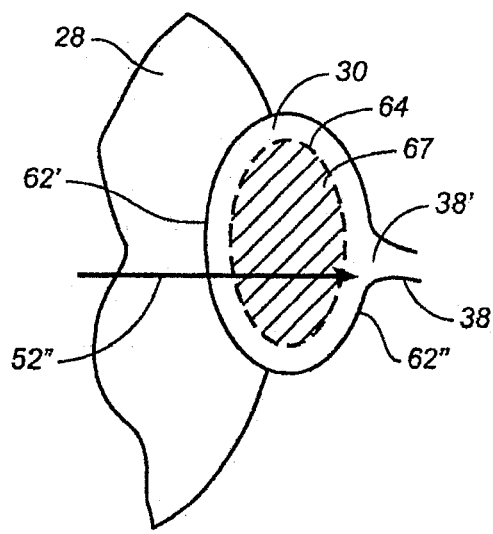
FIG. 4B shows a cross-sectional view along line I-I'.

Different fluid flow paths in and across Schlemm's canal are illustrated in FIGS. 4A-B. FIG. 4A shows a front view of an eye, and FIG. 4B shows an expanded cross-sectional view along line I-I'. Circumferential (i.e., longitudinal) flow along and around circular canal 30 is depicted by directional lines 50. Fluid that does not traverse canal 30 to reach collector channels 38 may not be effectively drained from the eye. Examples of fluid flow paths that can effectively drain the eye are illustrated by directional lines 52, 52', and 52". In each of these paths, fluid enters trabecular meshwork 28 along its inner peripheral surface 60 and exits the meshwork along its outer peripheral surface 62'. Meshwork outer peripheral surface 62' provides the inner peripheral surface or wall of Schlemm's canal 30. Transmural fluid flow across Schlemm's canal involves two instances of transmural flow across walls or boundaries. First, fluid must flow from trabecular meshwork 38 through inner peripheral surface or wall 62' of Schlemm's canal 30 to reach lumen 64 of the canal. Second, fluid must flow from lumen 64 through canal outer peripheral wall 62" through apertures 38' to enter collector channels 38. Finally, the collector channels 38 feed the drained fluid into vasculature. Lumen 64 of canal 30 includes a central core region 67. Thus, fluid flow from the eye differs from fluid flow in other vessels in the body where fluid need only flow longitudinally along the vessel, such as blood flowing through a vein.

Devices

Devices to reduce intraocular pressure comprising a support that can be implanted circumferentially in Schlemm's canal to maintain the patency of at least a portion of the canal are described here. The support occupies at least a portion of a central core of Schlemm's canal and does not substantially interfere with transmural flow across the canal. By "maintain the patency" of at least a portion the canal, it is meant that the support operates to keep the canal at least partially unobstructed to transmural flow, such that fluid can 1) exit through the trabecular meshwork; 2) traverse the canal; and 3) drain via the collector channels. To maintain the patency of the canal, it is not necessary that the support leave the canal unobstructed in regard to circumferential flow. By "does not substantially interfere" with transmural flow, it is meant that the support does not significantly block either fluid outflow from the trabecular meshwork or fluid outflow to the collector channels. In many variations, the support allows between about 0.1 and about 5 microliters per minute aqueous outflux from the eye through the trabecular meshwork and collector channels. The "central core of Schlemm's canal" refers to the region around the cross-sectional center of the canal in the interior space of the canal lumen, i.e., not on the periphery of the canal. Therefore, a device that occupies at least a portion of a central core of Schlemm's canal can traverse at least a portion of the canal's lumen.

Therefore, devices described here need not comprise an open-ended tubular support placed longitudinally along Schlemm's canal, i.e., the devices and supports can be non-tubular. A longitudinal, open-ended tubular support can enable longitudinal flow along the canal. However, even if fluid can flow longitudinally (i.e., circumferentially) along Schlemm's canal, the eye may not be effectively drained unless the fluid eventually traverses the canal. That is, transmural fluid flow across two boundaries must occur: 1) fluid must flow from the trabecular meshwork through a canal inner wall coincident with an outer peripheral boundary of the trabecular meshwork to reach the canal lumen; and 2) fluid must flow from the canal lumen through apertures in the canal outer peripheral wall to reach the connector channels. The collector channels are then able to further disperse the fluid and complete the natural draining process. A tubular support inserted longitudinally into the canal can have significant surface area overlap with surfaces of the canal such that transmural flow across the canal may be significantly impeded. A longitudinal tubular support placed in Schlemm's canal may block flow into the canal from the trabecular meshwork and block flow out of the canal into the collector channels.

Devices described herein for treating elevated intraocular pressure include a support that is implanted within Schlemm's canal. In many instances, the device will reduce the intraocular pressure by 1-40 mm Hg, for example by at least 2 mm Hg. In other instances, the device will reduce intraocular pressure by at least 4 mm Hg, or at least 6 mm Hg, or at least 10 or 20 mm Hg. In still other instances, the device will operate to bring the intraocular pressure into the range of about 8 to about 22 mm Hg. The support can be configured in a variety of ways to at least partially prop open Schlemm's canal thereby maintaining its patency without substantially interfering with or impeding transmural fluid flow across Schlemm's canal. In some variations, the support may interfere with or block longitudinal flow along or around the canal. In many instances, the support will be contained entirely within Schlemm's canal. In some variations the support will be implanted within the canal, but may extend partially beyond Schlemm's canal, e.g., into the trabecular meshwork.

In some variations, a support to maintain at least partial patency for Schlemm's canal to enable fluid flow between an inner wall of the canal and an outer wall of the canal can comprise elements or structures such as bead-like elements or beads, which can be connected together, e.g., as a string of beads. Individual elements or beads or a connected group of elements or beads can be inserted directly into Schlemm's canal. A more detailed description of supports incorporating elements or beads is provided below.

Figure 5A:
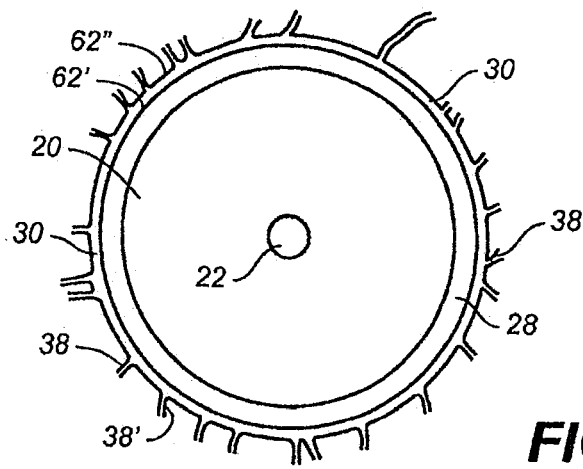
FIG. 5A provides a front view of an eye in which Schlemm's canal is narrowed or collapsed.

FIG. 5A illustrates a front view of an eye having a narrowed or collapsed Schlemm's canal 30, where canal outer peripheral wall 62" is very close to canal inner peripheral wall 62'. Although Schlemm's canal 30 is depicted in FIG. 5A as being uniformly narrow around the entire circumference of canal, it is possible that only a portion of Schlemm's canal is narrowed or collapsed. When Schlemm's canal is collapsed or narrowed, net efflux of aqueous from the anterior chamber to the collector channels 38 is diminished, thereby increasing intraocular pressure. As a result, the risk of pre-glaucoma, ocular hypertension, or glaucoma can increase.

Figure 5B:
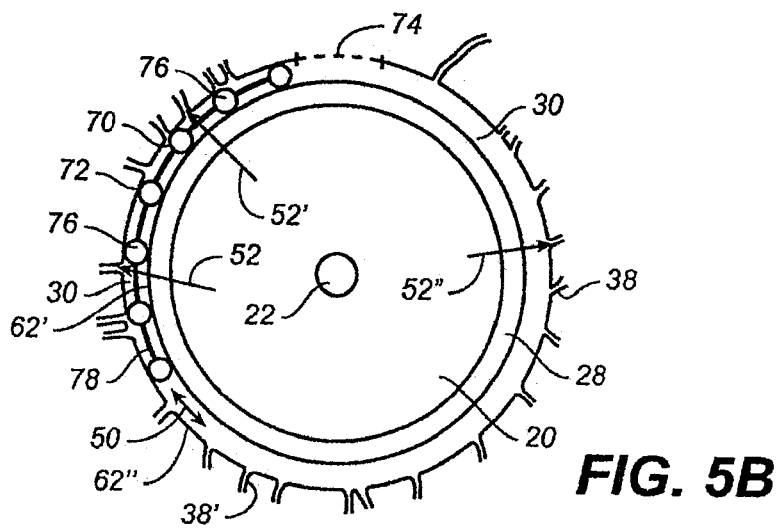
FIG. 5B shows a front view of a device including a support inserted into Schlemm's canal that allows transmural flow across the canal.

FIG. 5B illustrates an example of a device 70 inserted into Schlemm's canal 30 through incision site 74. Device 70 in this example is positioned to one side of incision site 74. Device 70 includes support 72 that is configured to keep Schlemm's canal at least partially open to transmural fluid flow across both canal inner wall 62' and canal outer wall 62" to reach collector channels 38 via apertures 38'. In the example shown in FIG. 5B, support 72 includes elements or beads 76 connected with connectors 78. In this variation, the distance between canal inner wall 62' and outer wall 62" is approximately determined by the cross-sectional dimension of support 72, which is in turn determined by the largest cross-sectional diameter of the beads 76. Therefore, circumferential (i.e., longitudinal) fluid flow around and along the canal 30 indicated by directional line 50 may be inhibited by the insertion of support 72 into the canal. However, transmural flow across both walls or boundaries of the canal indicated by directional lines 52, 52', 52" is enhanced by support 72 and fluid is able to reach collector channels 38 and be drained from the eye. As a result, support 72 can effectively reduce intraocular pressure by utilizing the eye's natural drainage mechanism. Incision 74 need only be large enough to accommodate the diameter of beads 76, so that trauma to the eye is minimized. Beads can have cross-sectional dimensions in the range from about 50 microns to about 500 microns. Insertion of beads having relatively small cross-sectional diameters (e.g., about 50 microns) into Schlemm's canal open the canal less than the normal cross-sectional diameter of the canal, which is about 190 to about 370 microns, but still can maintain the patency of the canal. Insertion of beads having relatively large cross-sectional diameters (e.g., greater than about 300 microns) can open the canal as large as or larger than the canal's normal cross-sectional diameter and also can operate to stretch the trabecular meshwork. Stretching the trabecular meshwork may further enhance drainage.

Figure 5C:
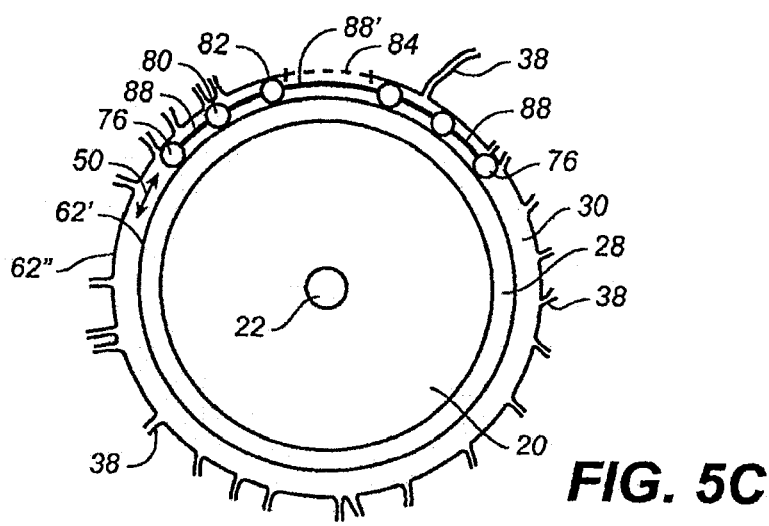
FIG. 5C illustrates an alternate design for a device inserted into Schlemm's canal that allows transmural flow across the canal.

FIG. 5C illustrates an alternate configuration of a device 80 inserted into Schlemm's canal 30 through incision site 84. Device 80 includes support 82 that extends to both sides of incision site 84. Support 82 includes elements or beads 76 connected with connectors 88 and 88'. In this example, connector 88' is of a different length than connectors 88. As in FIG. 5B, beads 76 may impede circumferential (i.e., longitudinal) fluid flow around and along canal 30 indicated by directional line 50. However transmural flow across the canal is enhanced by support 82 that maintains patency across the canal and allows fluid to reach collector channels 38. If the beads are fenestrated or comprise rough, spiked, or fluted perimeters, then circumferential fluid flow through or around the beads may also occur.

Figure 6A:
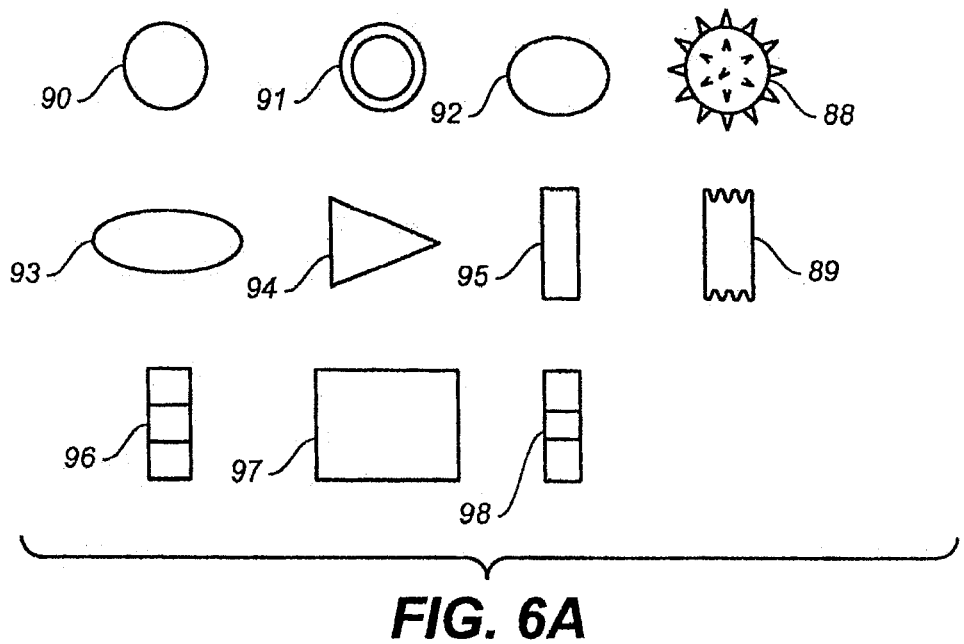
FIG. 6A shows side views of various element or bead configurations that can be used in the supports described herein.
Figure 6B:
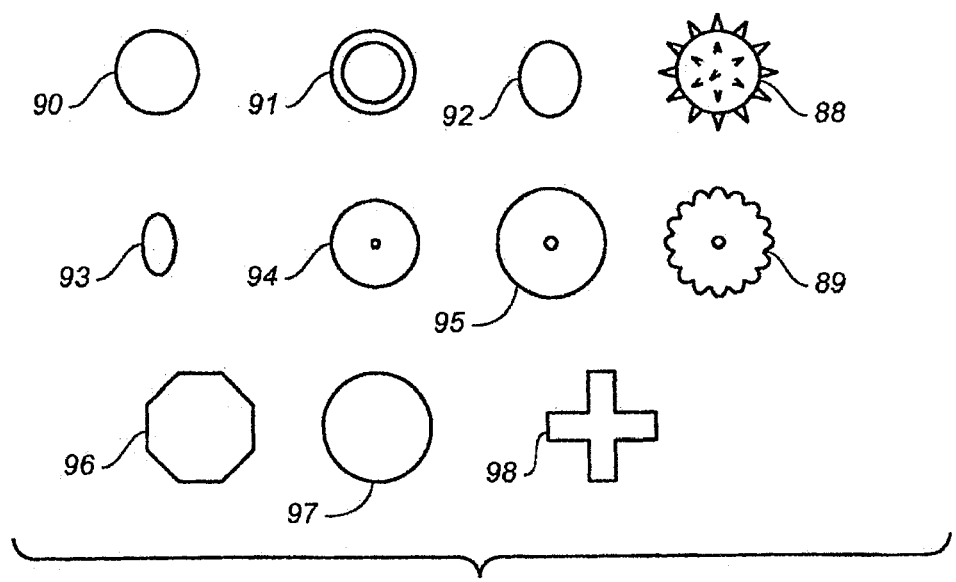
FIG. 6B shows the corresponding front views of the element or bead configurations shown in FIG. 6A.
Figure 6C:
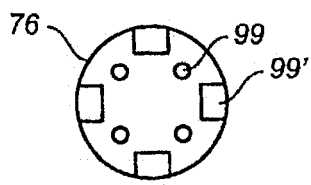
FIG. 6C illustrates an element or bead having fenestrations.

Elements or beads used in a support may be hollow and closed structures, open structures, solid structures, porous structures, or any combination thereof, and may be of any suitable shape. FIGS. 6A and 6B illustrate side and front views, respectively, of exemplary elements or beads that may be used in the supports described here. As shown, solid 90 or hollow 91, spherical 90, spheroid 92, ovoid 93, conical 94, disk-shaped 95, polyhedral 96, rod-like 97, or beads with fluted edges 98, rough edges, 89, or spiked edges 88 may be used. In some instances, it may be desired to round corners or edges of the beads. As illustrated in FIG. 6C, elements or beads 76 may include fenestrations 99, 99'. Fenestrations may have any suitable cross-sectional shape, such as round or quadrilateral. Although a disc-shaped bead 76 is shown in FIG. 6C, any shape of bead can be fenestrated.

Figure 7A:
FIG. 7A illustrates a support having multiple juxtaposed beads.
Figure 7B:
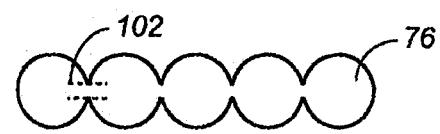
FIG. 7B illustrates a support having multiple juxtaposed and connected beads.
Figure 7C:
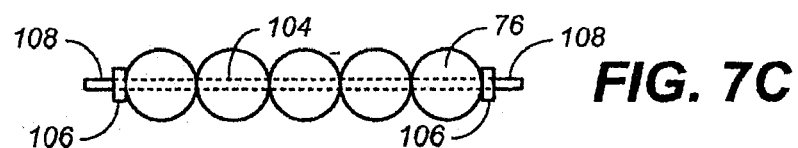
FIG. 7C shows an alternate configuration of a support having multiple juxtaposed and connected beads.
Figure 7D:
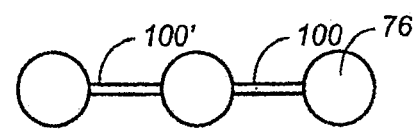
FIG. 7D shows a support having multiple, spaced-apart but connected beads.
Figure 7E:
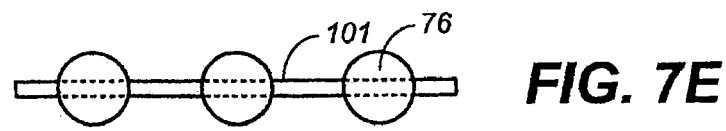
FIG. 7E illustrates beads threaded onto a connector.

As illustrated in the variations shown in FIGS. 7A-E, two or more beads 76 in a support may be adjacent to each other. Adjacent beads may be juxtaposed (FIG. 7A), connected and juxtaposed (FIGS. 7B and 7C), or connected together with connectors 100, 100' to form intervals between beads (FIG. 7D). In addition, beads may be threaded onto a connector 101 (FIG. 7E). Multiple beads used in a single support may have the same or different shapes, and may be made of the same or different materials.

Junctions 102 between beads as shown in FIG. 7B can be made using any suitable technique, such as by using an adhesive, chemical bonding, mechanical interlocking, or welding. Beads may also be juxtaposed and connected as shown in FIG. 7C by threading onto a guide element 104. Guide element 104 can comprise a fiber, a suture, a guide wire, a fixture, or the like. The beads can be fixed in a juxtaposed configuration on a guide element, e.g., by knotting ends of the fiber or by providing other end-blocking devices 106, such as clips, caps, protrusions, or the like on ends 108 of element 104. Any or all of the beads can be attached to guide element 104, e.g., beads occupying end positions may be attached to element 104 and function as blocking beads to keep beads from sliding off ends 108 of element 104. Alternatively, beads may slide along element 104. Guide element 104 can be flexible, such as thin polymer threads, such as a suture, or metal wires. Alternatively, element 104 can be flexible but fixable, such as one or more shapeable metal wires that can be bent into a desired position and maintain that position against some amount of external stress or pressure. In other variations, guide element 104 can be rigid, e.g., a molded polymeric piece or a stiff metal piece.

As shown in FIG. 7D, multiple connectors 100, 100' may be used in a single support, with at least one connector inserted between adjacent beads 76. If multiple connectors are used, they may be of the same or different lengths. In addition, multiple connectors within the same support may be made of the same or different materials, and the connectors may be made of the same or different materials than the beads. Discrete connectors 100, 100' can be inserted between beads 76 and attached to adjacent beads using any suitable method including using adhesives, chemical bonding, welding, mechanical interlocking, knots, or any combination thereof. In some variations, connectors 100, 100' between beads can be configured to function as spacers between individual beads. As illustrated in FIG. 7E, beads 76 can also be threaded onto a connector 101. If the beads are threaded onto a connector, the beads can be maintained in fixed positions along the connector 101 by any suitable method, including using adhesives, chemical bonding, welding, clips, protrusions on the connector, mechanical interlocking locking between a connector and a bead, knots, or any combination thereof. Alternatively, some or all beads may slide along connector 101. Connectors 100, 100', 101 can be flexible, such as thin polymer threads or metal wires. Connectors 100, 100', 101 can also be flexible but fixable, such as shapeable metal wires. Alternatively, connectors 100, 100', 101 may be rigid, such as molded polymeric connectors or stiff metal connectors.

Supports of the devices described here need not contain beads. For example, a support can be a unitary structure of fixed or variable length. Supports can be solid, hollow, or porous, or any combination thereof. For example, a support can be partially solid and partially hollow. Examples of support configurations are shown in side view and front view in FIGS. 8A-F. As illustrated in FIG. 8A-B, a support can have an open network structure. Such a support can be fabricated out of shapeable metal wires, for example. The support illustrated in FIGS. 8A-B will have minimal surface area contact with the walls of Schlemm's canal, i.e., only point contacts at the end of wires or fibers 170. Alternatively, a support having an open network structure can be at least partially made from a mesh or foam. The mesh or foam can be made of any suitable material, e.g., metal or plastic. As shown in FIGS. 8C-D, the support can have a sinusoidal or zig-zag configuration extending along a selected length of Schlemm's canal. For the example shown in FIG. 8C, the support will contact the wall of Schlemm's canal at at least three points, labeled $P_1$, $P_2$, and $P_3$, after implantation. In FIGS. 8E-H, examples of rod-like supports having fluted edges are shown. In FIGS. 8E-F, fluted edges 110 extend longitudinally along sides 112 between ends 114 of the support to form structures 116. Structures 116 can include fenestrations 113. The support can include central bore 117. In FIGS. 8G-H, fluted edges 110' extend along sides 112' to form structures 116'. Structures 116' have serrated outer surfaces 115' extending between ends 114'. The support can include central bore 117'. In the variations illustrated in FIGS. 8E-H, the support may contact the canal walls at at least four points. In some variations, the support is adjustable.

A common characteristic of the support configurations described here is that they need not have continuous or extensive contact with a wall of Schlemm's canal. Indeed, many of the described devices and structures have minimal tangential, periodic, or sporadic contact with the wall. The surface of the support can be rough, smooth, spiked or fluted. As the example shown in FIGS. 8A-B shows, some supports only have point contacts with the canal wall. For the supports shown in FIGS. 5B-C, the rounded beads of each of the supports make only tangential contact with the canal wall. Bead shapes can be selected or designed to have minimal surface area contact with canal walls, e.g., beads 98 having fluted edges as shown in FIGS. 6A-B may have low surface area contact with canal walls. In addition, supports having widely spaced apart beads, e.g., by connectors illustrated in FIGS. 7D-E that can function to space beads at desired intervals to reduce contact with canal walls yet operate to keep the canal open. As illustrated above with respect to FIGS. 8C-D, in some variations, the support contacts the interior wall of the canal at at least two points; or at at least three points.

Figure 9A:
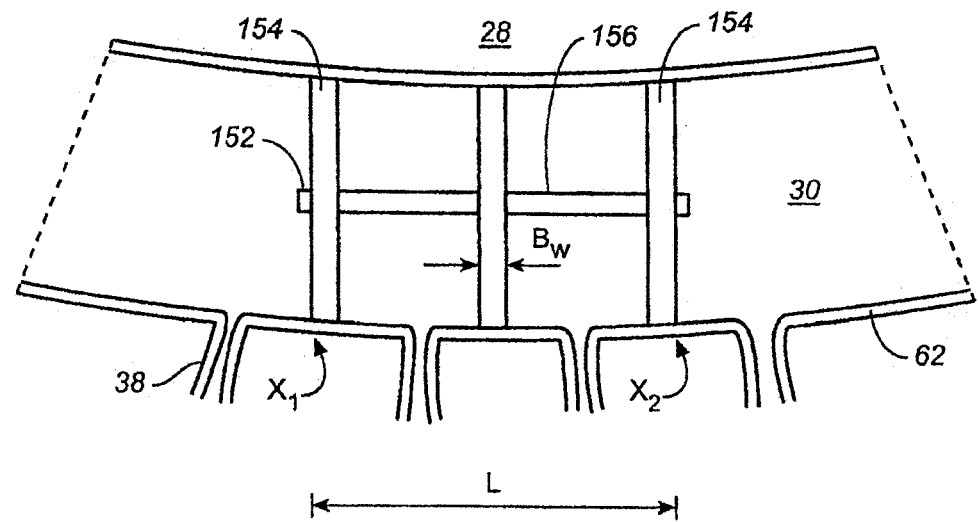
FIGS. 9A-B show expanded cross-sectional views of a support implanted within Schlemm's canal.
Figure 9B:
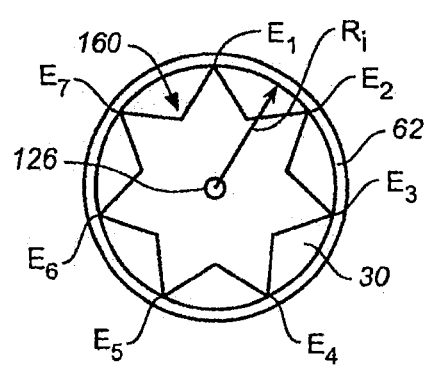

Expanded cross-sectional views of a support 152 implanted circumferentially in Schlemm's canal are provided FIGS. 9A-B. The fraction of canal wall surface area in contact with a support can be estimated by viewing the inside of Schlemm's canal as a slightly arcuate cylinder C having length L, extending circumferentially from a first end $X_1$ to a second end $X_2$ of support 152, and inside radius $R_i$. In some variations, the support contacts less than 0.1% or less than 1% of the surface area of the cylinder C as described above. In other variations, the support contacts less than 10% of the surface area of C. In still other variations, the support contacts less than 30% of the surface area of C. For example, the support 152 shown in FIGS. 9A-B contacts the canal wall 62 only at bead outer peripheral edges at $E_1$-$E_7$, along a distance of the bead width $B_W$. There is no contact with the canal walls where connectors 156 space apart beads 154, and no contact in fluted regions 160 of beads 154. The design feature of minimal support contact with canal walls allows a support to maintain patency of the canal without substantially interfering with transmural flow across the canal. If a substantial portion of the surface area of the inner periphery of the canal adjacent to the trabecular network or of the surface area of the outer periphery of the canal where the collector channels are located is blocked, effective fluid flow across the canal may be impaired.

Figure 10A:
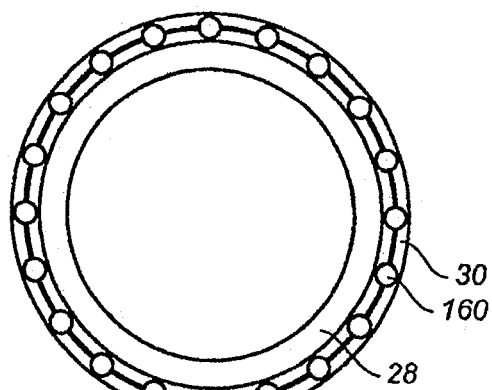
FIGS. 10A-C illustrate various configurations of supports implanted into Schlemm's canal.
Figure 10B:
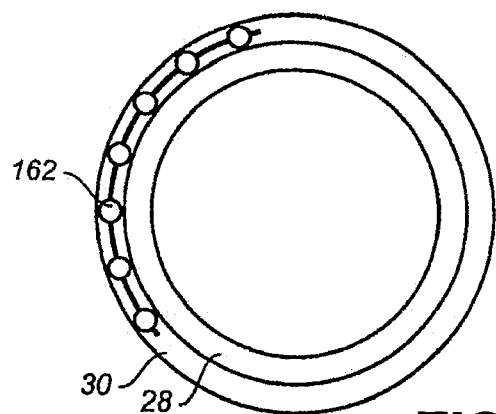
Figure 10C:
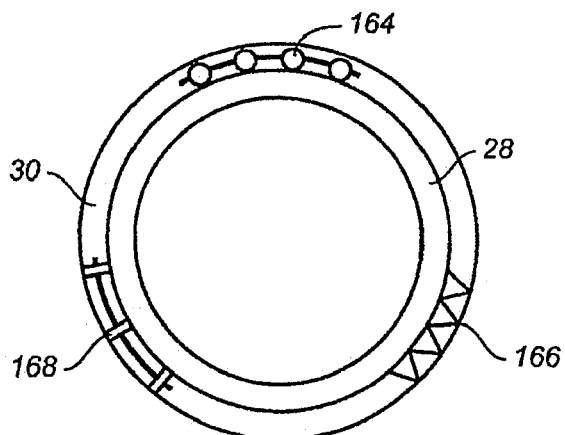

Supports can have variable lengths and thicknesses. For example, the length of supports using beads can be tuned by varying the number, type, or spacing of beads, or any combination thereof. The thickness of a support can be increased by adding one or more beads having larger dimensions. Unitary supports can also be built with varying lengths, or with adjustable (e.g., trimmable) dimensions. For example, for a support made of shapeable metal having a sinusoidal or zig-zag configuration as shown FIGS. 8C-D, a cross-sectional dimension 117 of the support can be decreased or increased by apply tension along dimension 119. As illustrated in FIG. 10A, a support 160 can extend essentially around the entire circumference of Schlemm's canal 30. Alternatively, a support can extend approximately half way around the circumference of the canal (not shown). As shown in FIG. 10B, a support 162 can extend less than half way around the canal. As shown in FIG. 10C, a support 164 can extend a quarter or less of the circumference around the canal. In addition, more than one support 164, 166, 168 can be inserted into a single Schlemm's canal. If multiple supports are inserted into a single canal, they can be of different shapes, lengths, materials or sizes.

Figure 11A:
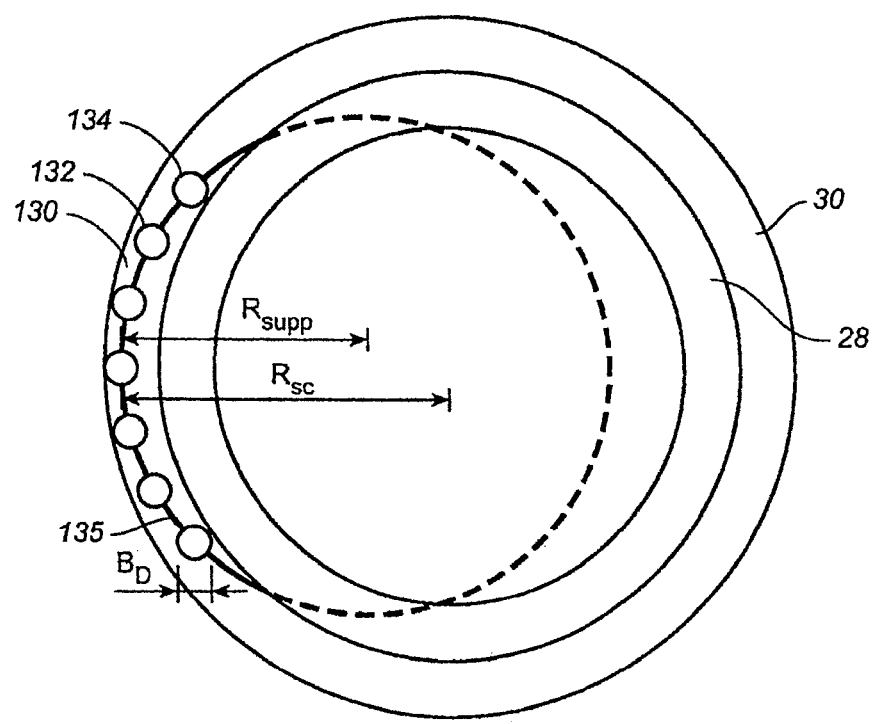
FIGS. 11A-B illustrate two configurations of supports having a smaller radius of curvature than Schlemm's canal.
Figure 11B:
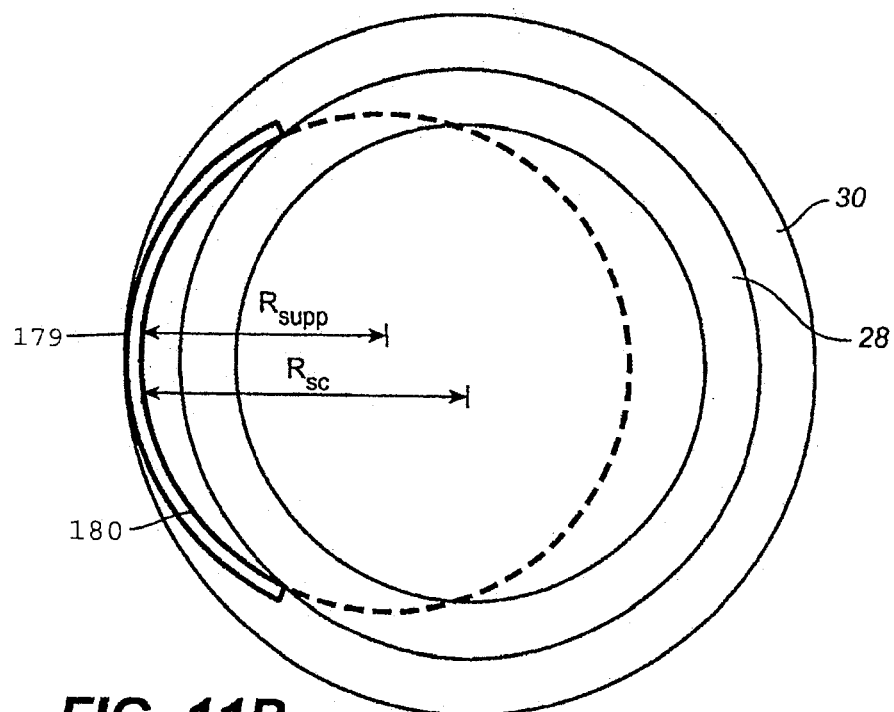
Figure 11C:
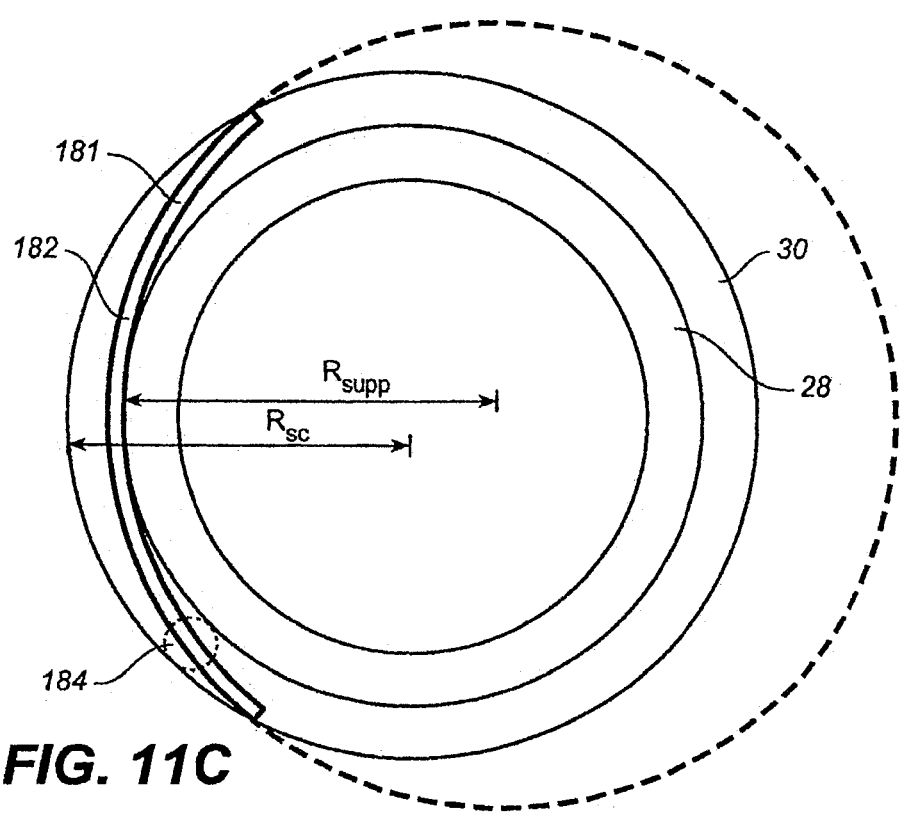
FIG. 11C shows a support having a larger radius of curvature than Schlemm's canal.

A support can be configured such that it will open the canal beyond a maximum cross-sectional dimension of the support itself. For example, as illustrated in FIG. 11A, device 130 comprising support 132 is inserted into Schlemm's canal 30. Support 132 comprises beads 134 which have a maximum cross-sectional dimension $B_D$. Support 132 comprises a stiff arcuate element 135 with a radius of curvature $R_{supp}$ smaller than the radius of curvature of Schlemm's canal $R_{SC}$. The smaller, fixed radius of curvature $R_{supp}$ of arcuate member135 urges canal 30 to open more than $B_D$. In another variation shown in FIG. 11B, support 179 comprises an arcuate member 180 without beads having a radius of curvature $R_{supp}$ that is less than the radius of curvature $R_{SC}$ of the canal. Member 180 is sufficiently stiff to urge the canal open. In another variation shown in FIG. 11C, support 181 comprises an arcuate member 182 having a radius of curvature $R_{supp}$ larger than that of Schlemm's canal $R_{SC}$. Member 182 is also sufficiently stiff to urge the canal open. Arcuate members 135, 180 and 182 can comprise a shape memory material such as Nitinol, for example. As indicated in FIG. 11C, support 181 can include beads 184. To urge open the canal, the radius of curvature $R_{supp}$ of an arcuate members can be about 10%, 20%, 30%, 40%, or 50% or smaller or larger than that of Schlemm's canal $R_{SC}$. For example, an arcuate member can have a radius of curvature of about 3 mm to about 8 mm. In some variations, the radius of curvature of an arcuate member $R_{supp}$ in a support is about 3 mm, or about 4 mm, or about 5 mm. In other variations, the radius of curvature $R_{supp}$ of an arcuate member in a support is about 6 mm, or about 7 mm, or about 8 mm.

The supports described here occupy at least a portion of a central core of Schlemm's canal. The central core of Schlemm's canal is the region around the cross-sectional center of the canal in the interior space of the canal lumen. A support that occupies at least a portion of the central core of the canal can traverse at least a portion of the canal lumen. For example, some variations of supports can traverse the cross-sectional center of the canal at at least one point. Referring to FIG. 12A, a front view of a support 220 having beads 222 connected with connectors 224 is provided. FIG. 12B shows an expanded cross-sectional view along line II-II'. Support 220 occupies a portion canal central core 67 in canal lumen 64. Trabecular meshwork 28 is shown adjacent to canal 30. In this variation, support 220 traverses the cross-sectional center 66 of the canal. In other variations, supports can traverse the lumen of the canal off-center, e.g., appearing as a chord across the canal lumen in cross-section. Referring to FIG. 12C, a front view of an arcuate support 210 is shown. FIG. 12D shows an expanded cross-sectional view along line III-III'. Support 210 traverses and occupies a portion of central core 67 in lumen 64 of canal 30 without passing through canal center 66. In some variations, the support can occupy the majority of the central core of the canal. Referring to FIG. 12E, a front view of support 230 comprising disc-like beads 232 is shown. A cross-sectional view along line IV-IV' is shown in FIG. 12F. As illustrated in FIG. 12F, bead 232 with fenestrations 234 occupies the majority of central core 67 of canal 30. In other variations, the support occupies only a small portion of the central core of the canal. For example, in FIG. 12G, a front view of a support 240 having an open network structure is shown. A cross-sectional view along line V-V' is shown in FIG. 12H.

A support can made of a variety of different materials. In general, the support should comprise a biocompatible material, such as a biocompatible polymer, ceramic or ceramic composite, glass or glass composite, metal, or combinations of these materials. Examples of biocompatible metals include stainless steel, gold, silver, titanium, tantalum, platinum and alloys thereof, cobalt and chromium alloys, and titanium nickel alloys such as Nitinol. Examples of biocompatible polymers include high density polyethylene, polyurethane, polycarbonate, polypropylene, polymethylmethacrylate, polybutylmethacryate, polyesters, polytetrafluoroethylene, silicone, polyvinyl alcohol, polyvinyl pyrrolidone, polyvinyl chloride, ethyl vinyl acetate, collagen, collagen derivatives, flexible fused silica, polyolefins, NYLON® polymer, polyimide, polyacrylamide, fluorinated elastomers, and copolymers and blends thereof. In addition, biocompatible hydrogels can be used in supports and devices described herein. As discussed in more detail below, biocompatible polymers may be biodegradable. A support can be made of a single material or a combination of materials. In some variations, a support made from a first material is coated with a second material, e.g., to enhance or improve its biocompatibility.

In some examples, the biocompatible polymer in a support will include a biodegradable polymer. Examples of suitable biodegradable polymers include collagen, a collagen derivative, a poly(lactide), a poly(glycolide), a poly(lactide-co-glycolide), a poly(lactic acid), a poly(glycolic acid), a poly(lactic acid-co-glycolic acid), a poly(lactide)/poly(ethylene glycol) copolymer, a poly(glycolide)/poly(ethylene glycol) copolymer, a poly(lactide-co-glycolide)/polyethylene glycol) copolymer, a poly(lactic acid)/poly(ethylene glycol) copolymer, a poly(glycolic acid)/poly(ethylene glycol) copolymer, a poly(lactic acid-co-glycolic acid)/poly(ethylene glycol) copolymer, a poly(caprolactone), a poly(caprolactone)poly(ethylene glycol) copolymer, a polyorthoester, a poly(phosphazene), a poly(hydroxybutyrate) or a copolymer including a poly(hdroxybutyrate), a poly(lactide-co-caprolactone), a polycarbonate, a poly(esteramide), a polyanydride, a poly(dioxanone), a poly(alykylene alkylate), a copolymer of polyethylene glycol and a polyorthoester, a biodegradable polyurethane, a poly(amino acid), a polyetherester, a polyacetal, a polycyanoacrylate, a poly(oxyethylene)/poly(oxypropylene) copolymer, and blends and copolymers thereof.

At least a portion of the support can be made from a shape memory material. For example, shape memory alloys, e.g. a nickel-titanium alloy can be used. In addition, shape memory polymers, e.g., polymers made from copolymerizing monomers oligo(e-caprolactone) dimethacrylate and n-butyl acrylate or polymers based on styrene acrylate, cyanate ester and epoxies, can be used. If a shape memory material is used in the support, the support can have a compressed state prior to and during implantation, and an expanded state following implantation. The use of a compressed state support comprising a shape memory material can allow for a smaller incision and facilitate insertion into a narrowed or compressed Schlemm's canal. Once implanted, the support can be expanding using any suitable method, e.g., thermally activated by body heat or an alternate heat source, to adopt an expanded state, thereby opening the canal.

The support can include an active agent, such as a pharmaceutical. Active agents can include prostaglandins, prostaglandin analogs, beta blockers, alpha-2 agonists, calcium channel blockers, carbonic anhydrase inhibitors, growth factors, such as tissue growth factors and vascular endothelial growth factors, anti-metabolites, chemotherapeutic agents such as mitomycin-C,5-fluorouracil, steroids, antagonists of growth factors such as antagonists of vascular endothelial growth factors, or combinations thereof. The active agent can be provided as a coating on at least a portion of a support. The active agent can be delivered throughout the eye by dissolution or other dispersal mechanisms. Alternatively, at least a portion of the support can be impregnated with the active agent. In other embodiments, the active agent can be dispersed within at least a portion of the support. For example, a cavity in the support can be filled with the active agent.

The delivery of the active agent can be controlled by time-release. For example, the portion of the support containing the active agent can include a time release coating or time release formulation designed to gradually dissipate the active agent over a certain period of time. Biodegradable coatings and formulations for time-release of active agents are known in the art. In some variations, the support can comprise multiple layers, where the layers each comprise an active agent. For example, support layers can be used to release a series of different agents, or a series of doses of the same agent. Such layers can be part of a coating applied to a support, or part of a support body. In addition, the support can comprise biodegradable layers containing no active agent that can be applied or interspersed between other layers to further control delivery of active agents to the eye.

Figure 13:
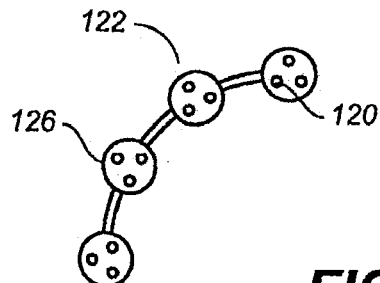
FIG. 13 shows an illustrative example of a support that can be modified using electromagnetic radiation.

In some variations, it will be desirable to change or alter the support using electromagnetic radiation. For example, at least a portion of a support can be fenestrated, perforated, bent, shaped or formed using a laser to enhance intraocular pressure reduction. As illustrated in FIG. 13, predetermined localized portions 120 of support 122 can be designed to absorb light of a certain wavelength or wavelength range. Preferential absorption can be achieved by material selection and/or by doping with chromophores. Upon irradiation with sufficient energy at the selected wavelength or wavelength range, the patterned regions 120 will ablate or melt, leaving new or enlarged perforations or indentations in the support. For example, a pulsed titanium sapphire laser operating between about 750 and about 800 nm can be used to ablate gold regions. If beads 126 in support 120 are hollow, then after irradiation and ablation, features 120 will become fenestrations. The fenestrations can be created to make support 122 more porous in nature or to allow release of an active agent from within a support, e.g., from within beads 126. Alternatively, it is possible to use a mask in combination with electromagnetic radiation to alter a support, such as by patterning or machining. The modification of a support using electromagnetic radiation can be carried out prior to or subsequent to insertion.

In some variations, the visual appearance of the support can be enhanced under certain conditions to facilitate placement or to monitor the position or condition of the support. Visual enhancement can be achieved by incorporating into or onto the support chromophores that fluoresce or phosphoresce upon excitation with a light source. Chromophores can also assist a clinician in verifying the position of the support postoperatively using a gonioscope, for example. Light sources can include lasers, lamps, and light emitting diodes. In some instances, transmission or absorption filters may be used to select the wavelength of the excitation source or to detect or view emission. Emission from a support capable of visual enhancement may be in the wavelength range of about 300 nm to about 800 nm. The chromophores can be an integral component of the material making up the support, doped into support material, or coated or sprayed onto the support. Visually-enhancing chromophores can be applied on a temporary basis, or on a permanent basis. An example of a suitable chromophore is fluorescein, which can be excited with any laser or lamp emitting at about 400 to about 500 nm. In addition, phosphorus-based chemiluminescent or photoluminscent pigments can be used, which can be selected to absorb at various wavelengths across the visible spectrum.

In some variations, the support may be capable of being attached to tissue. For example, the support may include a hook, loop, clip, extension, or the like that may be easily attached to tissue. The support may also be attached to tissue using sutures or adhesives. The support may be attached to tissue using more than one attachment method, e.g., suturing may be used in combination with a loop, or an adhesive may be used in combination with a hook. In other variations, the support may be allowed to self-position in Schlemm's canal. In still other variations, the support may be mobile within Schlemm's canal.

Kits

Kits for reducing intraocular pressure are provided, where the kits contain at least one support that can be implanted circumferentially within Schlemm's canal configured to maintain the patency of at least a portion of Schlemm's canal. The support occupies at least a portion of a central core of Schlemm's canal and does not substantially interfere with transmural flow across the canal. The kits also provide an introducer or delivery device for implanting the support in the canal. The support and introducer are provided in packaged combination in the kits. The kits can also include instructions for use, e.g., for implanting and inspecting the support.

The introducer can be inserted into the eye and is capable of implanting the support at the desired implantation position within Schlemm's canal. For example, an introducer may include a tubular cannula through which the support may be passed. In addition to a cannula, the introducer may include a tubular or solid pusher rod that can be used to push or advance the support into and/or around Schlemm's canal. Alternatively, a pusher rod or plunger can be used without a cannula to introduce a support into the canal. A support can be installed into the lumen of a cannula prior to insertion, the distal end of the cannula positioned at or near the desired support location, and the pusher rod operated from the proximal end to push the support distally out of the distal end of the cannula and into the canal. The cannula and/or the pusher rod may be flexible and small enough in diameter to extend at least partially around the canal. In some variations, a proximal end of a suture can be introduced into the canal via a cannula and the suture extended circumferentially around the canal. A distal portion of the suture can be connected to the support and force applied to the proximal end of the suture to pull the support into the canal. The support can then be positioned within the canal by pulling the suture in a distal or proximal direction. The suture can be used to anchor the support within the canal. In other variations, the support can be directly introduced into the canal using surgical forceps, or the like.

Figure 14A:
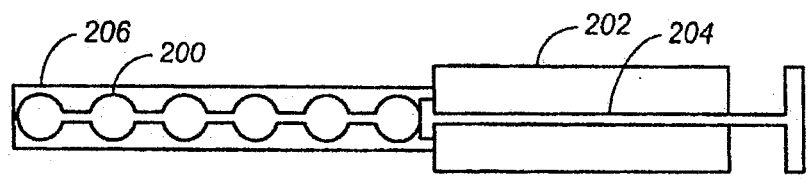
FIG. 14A illustrates a syringe that can be used to insert a support into Schlemm's canal.
Figure 14B:
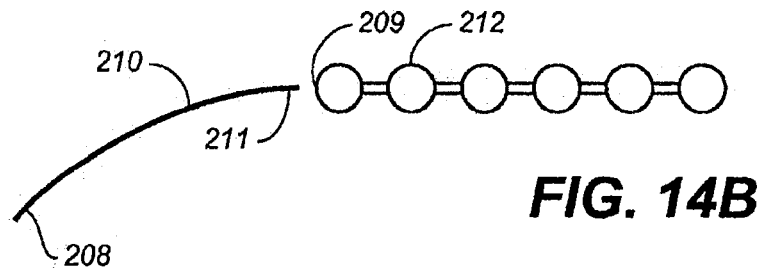
FIG. 14B illustrates a variation in which a support is threaded onto a guide element for insertion and positioning in Schlemm's canal.
Figure 14C:
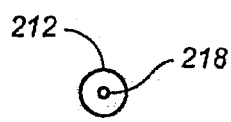
FIG. 14C illustrates a cross-sectional view of a support having a central bore to accommodate a guide element.
Figure 14D:
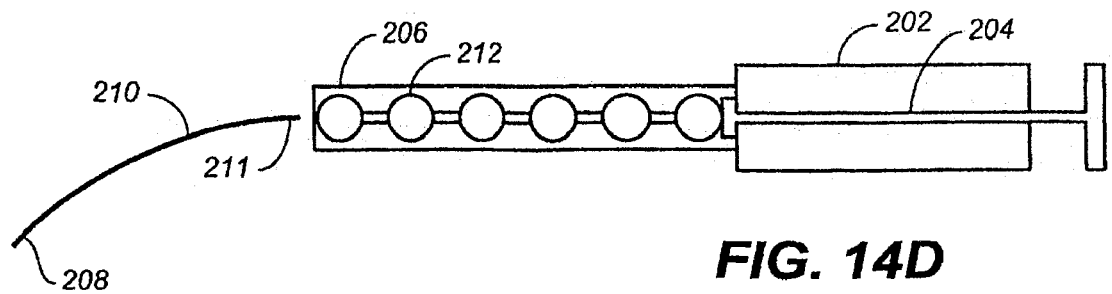
FIG. 14D illustrates a variation in which a syringe and a guide element are used for insertion and positioning of a support in Schlemm's canal.

FIGS. 14A-D illustrate additional variations for introducing a support into the canal. As shown in FIG. 14A, a support 200 can be introduced into the canal using syringe 202 and plunger 204. Syringe 202 has distal end 206 that can be at least partially inserted into or placed adjacent to an opening in the canal. Force in a distal direction is applied to plunger 204, thereby pushing support 200 into the canal. Referring to FIGS. 14B-C, distal end 208 of guide element 210 can be at least partially introduced into the canal. Guide element 210 can be a guide wire. Guide element 210 can be extended circumferentially along the canal to aid in positioning the support. Support 212 comprises central bore 218 capable of accommodating guide element 210 such that support 212 can be threaded onto guide element 210 and slidably positioned along the guide element. Once distal end 209 of support 212 is threaded onto guide element 210, support 212 can be pushed in a distal direction along guide element 210 to insert support 212 into the canal. In some variations, support 212 can remain threaded onto guide element 210, and guide element 210 can remain in the canal. In other variations, support 212 can be slid off distal end 208 of guide element 210, and the guide element can be pulled in a proximal direction for removal. Referring to FIGS. 14C-D, syringe 202 with plunger 204 can be used in combination with a guide element 210. In this variation, distal end 208 of guide element 210 is inserted at least partially into Schlemm's canal. Guide element 210 can be extended circumferentially along the canal to aid in positioning the support. Support 212 has central bore 218 capable of accommodating guide element 210. Proximal end 211 of guide element 210 is inserted into bore 218. Plunger 204 is depressed in a distal direction to push support 212 into the canal and slide support 212 along element 210. Guide element 210 can remain in the canal or be removed following insertion of the support. Supports 200, 212 must be sufficiently resilient to withstand force encountered as they are pushed into the canal.

In some variations, a positioning device may be used with the introducer to position or adjust the support within the canal. A positioning device can include a rod, grippers, a clamp, a hook, or the like. In other variations, a device or system capable of dilating the canal to facilitate insertion of a support may be included in the kits, e.g., a syringe or other device capable of injecting fluid into the canal.

In some variations, the kits contain at least two supports. Multiple supports can be implanted within one eye or within multiple eyes. If the kits contain multiple supports, the kits may also contain multiple introducers. Alternatively, the same introducer may be used for implantation of multiple supports, especially if the multiple supports are being delivered to a single eye. If multiple supports are to be delivered with the same introducer, then the multiple supports can be preloaded into the introducer for sterility. If more than one support is included in a kit, the supports may be of different shapes, sizes, lengths, or materials. If the kits contain more than one support to be implanted into a single eye, the supports can be connected together.

The kits can comprise an active agent, such as a pharmaceutical agent. The active agent may be included as an integral part of the support, or may be supplied in kits for application to the support or to the eye during or after implantation. Examples of active agents that may be supplied as part of the kits include prostaglandins, prostaglandin analogs, beta blockers, alpha-2 agonists, calcium channel blockers, carbonic anhydrase inhibitors, growth factors, such as tissue growth factors or vascular endothelial growth factors, anti-metabolites, chemotherapeutic agents such as mitomycin-C,5-fluorouracil, steroids, antagonists of growth factors, such as antagonists of vascular endothelial growth factor, and combinations thereof.

The kits may contain a fixation device for attaching a support to tissue. Such a fixation device can include sutures, hooks, barbs, clips, adhesives, and combinations thereof. In addition, the kits may include a system for visually enhancing the support to facilitate viewing, positioning, and monitoring of a support. A system for visually enhancing the support can include a light source, a transmission or absorption filter, a mirror, a composition comprising a chromophore capable of fluorescing or phosphorescing that can be applied to the support, or any combination thereof. Chromophores can assist a clinician in verifying the position of the support postoperatively using a gonioscope, for example. The light source is capable of exciting a chromophore contained within or on the support such that the chromophore emits fluorescence or phosphorescence. The emission is preferably within the wavelength range of about 300 nm to about 800 nm. A suitable light source for such a system can comprise a laser, a light emitting diode, or a lamp. In some instances, transmission or absorption filters may be used to further select the wavelength range of the excitation source or view or detect emission from chromophores. One or more mirrors may be used to direct a light source or emitted light, or to view the support.

Methods

Methods for reducing intraocular pressure are also provided. In general, the methods comprise inserting a support circumferentially within Schlemm's canal, such that the support maintains the patency of at least a portion of the canal. The support occupies at least a portion of a central core of Schlemm's canal and does not substantially interfere with transmural flow across Schlemm's canal.

The methods can comprise inserting a support circumferentially into Schlemm's canal using an introducer and/or a positioning device. The introducer can include a cannula and a tubular or hollow pusher rod. The support can be installed in the lumen of the cannula at its distal end and the pusher rod can be inserted into the lumen of the cannula at its proximal end and extended distally to push the support into position in the canal. In some instances, the cannula and/or the pusher rod may be flexible and small enough in diameter to at least partially extend circumferentially around the canal. In some variations of the methods, a positioning device can be used in addition to an introducer. The positioning device can comprise a second rod, a gripper, a hook, a clamp, or the like. In some variations, the methods include illuminating a support with a light source to causes the support to fluoresce or phosphoresce, thus aiding the visual appearance of the support. The illuminating of the support can occur during or after implantation to inspect the support, e.g., to monitor its position, condition, or performance.

In some instances, the methods will also comprise dilating Schlemm's canal prior to insertion of the support. Dilation of the canal can be accomplished by injecting fluid into the canal. For example, a high viscosity fluid such as sodium hyaluronate, or other dilating fluids known in the art, can be used to dilate the canal.

The methods may include implanting more than one support into an eye. In some variations, the methods will include implantation of two or more supports circumferentially adjacent to each other within the canal, and in other variations, the methods will include implantation of supports circumferentially opposed to each other within the canal, e.g., two supports centered about 180° apart around the circumference of Schlemm's canal. Some variations of the methods can comprise connecting together multiple supports in a single eye.

In some variations, the methods can include anchoring the support to tissue surrounding Schlemm's canal. Anchoring the support to tissue can be accomplished in a variety of ways, e.g., by suturing, application of adhesives, installation of hooks, clips, or the like, or combinations thereof. In other variations, the methods can comprise selecting the size of the support such that the support fits securely into the canal by a friction fit. Examples of arcuate supports that can be implanted with a friction fit are illustrated in FIGS. 11A-C.

The methods described here can also include altering the support using electromagnetic radiation. For example, a support can include regions capable of preferentially absorbing a certain wavelength range. When electromagnetic radiation of the appropriate wavelength range with sufficient energy is incident upon the support, material in the preferentially absorbing regions will melt or ablate, resulting in perforations or indentations in the support at those regions. For example, a pulsed titanium sapphire laser emitting at about 750 nm to about 800 nm incident on gold can cause the gold to melt or ablate. The alteration of the support using electromagnetic radiation can occur before or after implantation of a support. For example, fenestrations can be created or enlarged in a support after the support has remained in an eye for a period of time to enhance drainage.

While the inventive devices, kits and methods have been described in some detail by way of illustration, such illustration is for purposes of clarity of understanding only. It will be readily apparent to those of ordinary skill in the art in light of the teachings herein that certain changes and modifications may be made thereto without departing from the spirit and scope of the appended claims. For example, it is envisioned that the devices, kits and methods can be applied to nonhuman eyes to reduce intraocular pressure, e.g., in dogs, cats, primates, or horses.

What we claim is:

1. A method for treating a condition of the eye, comprising:
   delivering a high viscosity fluid into Schlemm's canal;
   inserting a distal end of an introducer into Schlemm's canal; and
   placing a support in Schlemm's canal by operating the introducer.

2. The method of claim 1, wherein the introducer comprises a pusher rod.

3. The method of claim 2, wherein the support is advanced by operating the pusher rod from a proximal end of the introducer.

4. The method of claim 1, further comprising anchoring the support to tissue surrounding Schlemm's canal.

5. The method of claim 1, further comprising using a gonioscope.

6. The method of claim 1, further comprising adjusting the position of the support using a positioning device.

7. The method of claim 1, wherein the support extends about a quarter or less than a quarter of the circumference of Schlemm's canal after placement.

8. The method of claim 1, wherein at least a portion of the support extends out of Schlemm's canal after placement.

9. The method of claim 1, wherein the support does not substantially interfere with longitudinal flow along the canal after placement.

10. The method of claim 1, wherein the support enhances transmural flow across the wall of the canal after placement.

11. The method of claim 1, wherein the support extends circumferentially along Schlemm's canal after placement.

12. The method of claim 1, wherein when the support is disposed within a cylindrical section of the lumen of Schlemm's canal having an internal wall surface area C, the support contacts less than 30% of C.

13. The method of claim 1, wherein when the support is disposed within a cylindrical section of the lumen of Schlemm's canal having an internal wall surface area C, the support contacts less than 10% of C.

14. The method of claim 1, wherein the high viscosity fluid is sodium hyaluronate.

15. The method of claim 1, wherein at least a portion of the support is made from a shape memory material.

16. The method of claim 15, wherein the shape memory material comprises a shape memory alloy.

17. The method of claim 16, wherein the shape memory alloy comprises a nickel titanium alloy.

18. The method of claim 1, wherein the support is flexible.

19. The method of claim 1, wherein the support comprises a central bore.

20. The method of claim 1, wherein the support comprises at least one fenestration.

\* \* \* \* \*